United States Patent
Briggs et al.

(10) Patent No.: US 12,137,949 B2
(45) Date of Patent: Nov. 12, 2024

(54) RIB FRACTURE FIXATION DEVICE AND METHODS FOR USE THEREOF

(71) Applicant: Sanford Health, Sioux Falls, SD (US)

(72) Inventors: Steven Briggs, Sioux Falls, SD (US); Patrick W. Kelly, Sioux Falls, SD (US)

(73) Assignee: Sanford Health, Sioux Falls, SD (US)

( * ) Notice: Subject to any disclaimer, the term of this patent is extended or adjusted under 35 U.S.C. 154(b) by 861 days.

(21) Appl. No.: 17/283,522

(22) PCT Filed: Oct. 14, 2019

(86) PCT No.: PCT/US2019/056102
§ 371 (c)(1),
(2) Date: Apr. 7, 2021

(87) PCT Pub. No.: WO2020/077337
PCT Pub. Date: Apr. 16, 2020

(65) Prior Publication Data
US 2021/0386461 A1  Dec. 16, 2021

Related U.S. Application Data

(60) Provisional application No. 62/903,131, filed on Sep. 20, 2019, provisional application No. 62/900,332, (Continued)

(51) Int. Cl.
*A61B 17/72* (2006.01)
*A61B 17/00* (2006.01)
(Continued)

(52) U.S. Cl.
CPC ...... *A61B 17/7208* (2013.01); *A61B 17/1633* (2013.01); *A61B 17/1642* (2013.01);
(Continued)

(58) Field of Classification Search
CPC ............ A61B 17/7208; A61B 17/1633; A61B 17/1642; A61B 17/7225; A61B 17/7275;
(Continued)

(56) References Cited

U.S. PATENT DOCUMENTS 9,848,930 B2   12/2017   Huebner
2007/0233105 A1*  10/2007  Nelson ............... A61B 17/7266
606/64

(Continued)

OTHER PUBLICATIONS

International Search Report and Written Opinion for corresponding PCT application No. PCT/US2019/056102, dated Mar. 24, 2020.

*Primary Examiner* — Nicholas J Plionis
(74) *Attorney, Agent, or Firm* — McDonnell Boehnen Hulbert & Berghoff LLP

(57) ABSTRACT

The disclosure provides example methods, systems and apparatus for stabilization of a rib. An example method includes: (a) accessing a medullary canal of a rib having a fracture, (b) advancing a guidewire into the medullary canal across the fracture, (c) advancing a delivery catheter containing a stent over the guidewire into the medullary canal and across the fracture, (d) retracting the delivery catheter relative to the stent, and (e) expanding the stent in the medullary canal.

17 Claims, 19 Drawing Sheets

Related U.S. Application Data filed on Sep. 13, 2019, provisional application No. 62/744,906, filed on Oct. 12, 2018.

(51) Int. Cl.
  *A61B 17/16* (2006.01)
  *A61B 17/32* (2006.01)
  *A61B 17/80* (2006.01)
  *A61B 17/88* (2006.01)

(52) U.S. Cl.
  CPC ...... *A61B 17/7225* (2013.01); *A61B 17/7275* (2013.01); *A61B 17/8076* (2013.01); *A61B 17/8858* (2013.01); *A61B 2017/00004* (2013.01); *A61B 17/32* (2013.01); *A61B 2017/320044* (2013.01)

(58) Field of Classification Search
  CPC . A61B 17/8076; A61B 17/8858; A61B 17/32; A61B 2017/320044
  See application file for complete search history.

(56) References Cited

U.S. PATENT DOCUMENTS

| | | | |
|---|---|---|---|
| 2008/0255560 A1* | 10/2008 | Myers | A61B 17/7225 607/51 |
| 2009/0216232 A1 | 8/2009 | Buford | |
| 2015/0374411 A1 | 12/2015 | Ehmke | |

* cited by examiner

```
                                              ┌─ 300
                                              ▼
    ┌─ 305
┌───┴──────────────────────────────────────────────────────┐
│ Creating a first access hole through a cortex of a rib   │
│ on a first side of a fracture to a medullary canal of    │
│ the rib                                                  │
└──────────────────────────────┬───────────────────────────┘
                               ▼
    ┌─ 310
┌───┴──────────────────────────────────────────────────────┐
│ Creating a second access hole through the cortex of the  │
│ rib on a second side of the fracture to the medullary    │
│ canal                                                    │
└──────────────────────────────┬───────────────────────────┘
                               ▼
    ┌─ 315
┌───┴──────────────────────────────────────────────────────┐
│ Accessing the medullary canal through the first access   │
│ hole, via a first wire having a first reciprocal coupling│
│ at free end of the first wire                            │
└──────────────────────────────┬───────────────────────────┘
                               ▼
    ┌─ 320
┌───┴──────────────────────────────────────────────────────┐
│ Accessing the medullary canal through the second access  │
│ hole, via a second wire having second reciprocal coupling│
│ at a free end of the second wire                         │
└──────────────────────────────┬───────────────────────────┘
                               ▼
    ┌─ 325
┌───┴──────────────────────────────────────────────────────┐
│ Advancing the free end of the first wire and the free    │
│ end of the second wire through the medullary canal until │
│ the first reciprocal coupling and the second reciprocal  │
│ coupling engage with each other thereby providing a      │
│ through-and-through wire                                 │
└──────────────────────────────┬───────────────────────────┘
                               ▼
    ┌─ 330
┌───┴──────────────────────────────────────────────────────┐
│ Advancing a tension line through the first access hole   │
│ into the medullary canal across the fracture and out the │
│ second access hole, wherein the tension line comprises a │
│ wire disposed through an alternating plurality of rods   │
│ and beads arranged in series along at least a portion of │
│ the length of the tension line                           │
└──────────────────────────────┬───────────────────────────┘
                               ▼
    ┌─ 335
┌───┴──────────────────────────────────────────────────────┐
│ Placing the tension line under tension                   │
└──────────────────────────────────────────────────────────┘
```

FIG. 8

RIB FRACTURE FIXATION DEVICE AND METHODS FOR USE THEREOF

CROSS REFERENCE TO RELATED APPLICATION

This application is a U.S. National Phase application of, and claims the benefit of, International (PCT) Application No. PCT/US2019/056102, filed Oct. 14, 2019, which claims priority to (i) U.S. Provisional Application No. 62/744,906 entitled "Rib Fracture Fixation Device and Methods for Use Thereof," filed on Oct. 12, 2018, (ii) U.S. Provisional Application No. 62/900,332 entitled "Rib Fracture Fixation Device and Methods for Use Thereof," filed on Sep. 13, 2019, and (iii) U.S. Provisional Application No. 62/903,131 entitled "Rib Fracture Fixation Device and Methods for Use Thereof," filed on Sep. 20, 2019, the contents of all of which are hereby incorporated by reference in their entirety.

BACKGROUND

Rib fractures were previously treated with only drugs. Subsequently, surgical management of rib fractures developed that involves an open technique cutting through muscle and skin with large incisions to screw plates into the fractured ribs to stabilize the bone.

SUMMARY

In one aspect, an example method is disclosed. The method includes (a) accessing a medullary canal of a rib having a fracture, (b) advancing a guidewire into the medullary canal across the fracture, (c) advancing a delivery catheter containing a stent over the guidewire into the medullary canal and across the fracture; (d) retracting the delivery catheter relative to the stent; and (e) expanding the stent in the medullary canal.

In another aspect, an example method is disclosed. The method includes (a) creating a first access hole through a cortex of a rib on a first side of a fracture to a medullary canal of the rib, (b) creating a second access hole through the cortex of the rib on a second side of the fracture to the medullary canal, (c) accessing the medullary canal through the first access hole, via a first wire having a first reciprocal coupling at free end of the first wire, (d) accessing the medullary canal through the second access hole, via a second wire having second reciprocal coupling at a free end of the second wire, (e) advancing the free end of the first wire and the free end of the second wire through the medullary canal until the first reciprocal coupling and the second reciprocal coupling engage with each other thereby providing a through-and-through wire, (f) advancing a tension line through the first access hole into the medullary canal across the fracture and out the second access hole, wherein the tension line comprises a wire disposed through an alternating plurality of rods and beads arranged in series along at least a portion of the length of the tension line, and (g) placing the tension line under tension.

In another aspect, an example method is disclosed. The method includes (a) creating a first access hole through a cortex of a rib on a first side of a fracture to a medullary canal of the rib, (b) accessing the medullary canal through the first access hole, (c) advancing a catheter through the first access hole into the medullary canal across the fracture; and (d) injecting the medullary canal with a polymer.

In still another aspect, an example method is disclosed. The method includes (a) creating a first access hole through a cortex of a rib on a first side of a fracture to a medullary canal of the rib, (b) creating a second access hole through the cortex of the rib on a second side of the fracture to the medullary canal, (c) accessing the medullary canal through the first access hole, via a catheter, (d) advancing the catheter across the fracture, (e) advancing the free end of a tension line out of the catheter and into the medullary canal; where the tension line has a snare at the free end, (f) accessing the medullary canal through the second access hole, via an extractor, (g) engaging the snare of the tension line with a hook of the extractor and advancing the free end of the tension line out of the second access hole such that the tension line extends through the first access hole into the medullary canal across the fracture, where the tension line has threads, (h) removing the snare from the free end of the tension line, (i) advancing a first plug down the free end of the tension line and into the second access hole, wherein the first plug has a hole extending longitudinally therethrough that has reciprocal threads to mate with the threads of the tension line; and (j) placing the tension line under tension.

In another aspect, an example system is disclosed. The system includes (a) a tension line having a removable snare at a free end, where the tension line has threads, (b) a first plug configured to be advanced down the free end of the tension line and a second access hole of a rib, where the first plug has a hole extending longitudinally therethrough that has reciprocal threads to mate with the threads of the tension line, (c) a plurality of stents configured to be advanced over the tension line through a first access hole in a rib into the medullary canal of the rib until a length of the medullary canal between the first access hole and the second access hole is filled with the plurality of stents, where each of the plurality of stents has a concave face at a first end and a convex face at a second end such that, when the plurality of stents are arranged adjacent to each other along the tension line, the concave face of the first end of a first stent will mate with the convex face of the second end of an adjacent second stent, and (d) a second plug configured to be advanced down an end of the tension wire and into the first access hole, where the second plug has a hole extending longitudinally therethrough that has reciprocal threads to mate with the threads of the tension line.

In yet another aspect, an example method is disclosed. The method includes (a) creating a first access hole through a cortex of a rib on a first side of a fracture to a medullary canal of the rib, (b) creating a second access hole through the cortex of the rib on a second side of the fracture to the medullary canal, (c) accessing the medullary canal through the first access hole, via a catheter, (d) advancing the catheter across the fracture, (e) advancing the free end of a tension line out of the catheter and into the medullary canal; wherein the tension line has a snare at the free end, (f) accessing the medullary canal through the second access hole, via an extractor, (g) engaging the snare of the tension wire with a hook of the extractor and advancing the free end of the tension line out of the second access hole such that the tension line extends through the first access hole into the medullary canal across the fracture, where the tension line has threads, (h) removing the snare from the free end of the tension line, and (i) advancing a stent over the tension line through the first access hole and the medullary canal to the second access hole, where the stent has a hole extending longitudinally therethrough that has reciprocal threads to mate with the threads of the tension line.

In another aspect, an example method is disclosed. The method includes (a) creating a first access hole through a cortex of a rib on a first side of a fracture to a medullary canal of the rib, (b) accessing the medullary canal through the first access hole, (c) advancing a catheter through the first access hole into the medullary canal across the fracture to a distal end of the medullary canal, and (d) advancing a guidewire through the catheter distal to the fracture in the medullary canal and securing an anchor coupled to a distal end of the guidewire within the medullary canal, where the guidewire is configured as a tension line.

In still another aspect, an example method is disclosed. The method includes (a) creating a first access hole through a cortex of a rib on a first side of a fracture to a medullary canal of the rib, (b) advancing a first portion of a first drill bit through the first access hole into the medullary canal across the fracture to a position distal to the fracture in the medullary canal where the first drill bit has a plurality of notches configured to permit detachment from a drill, (c) applying a force to the first drill bit and thereby causing a fracture along one of the plurality of notches, and (d) detaching a second portion of the first drill bit from the first portion of the first drill bit in the medullary canal.

In another aspect, an example apparatus is disclosed. The apparatus includes a drill bit having a first portion and a second portion, where the first portion of the drill bit has threads disposed along a length of the first portion, where the second portion of the drill bit has a plurality of notches along a length of the second portion, the plurality of notches configured to permit detachment from a drill upon application of a force to the drill bit such that a fracture is caused along one of the plurality of notches, where the first portion of the drill bit and one or more notches of the second portion of the drill bit are configured to remain in a medullary canal of a rib.

In yet another aspect, an example method is disclosed. The method is for placement of a rib plate having a first portion and a second portion each having a plurality of holes therethrough and a third portion arranged between the first portion and the second portion, the third portion of the rib plate having a hole configured to receive a protuberance coupled to a porous tube that has two open ends. The method includes (a) coupling the rib plate to the porous tube, (b) placing bone graft in a lumen of the porous tube, (c) implanting the tube in a gap between a first segment of a rib and a second segment of the rib, and (d) anchoring the first portion and the second portion of the rib plate to the first segment and the second segment of the rib such that the porous tube is aligned with the first segment and the second segment of the rib.

In another aspect, an example system is disclosed. The system includes (a) a rib plate having a first portion and a second portion each having a plurality of holes therethrough and a third portion arranged between the first portion and the second portion, (b) a porous tube that has two open ends and a protuberance arranged between the two ends that extends from an exterior surface of the porous tube, wherein the third portion of the rib plate has a hole configured to receive the protuberance of the porous tube; and (c) bone graft disposed in a lumen of the porous tube.

The features, functions, and advantages that have been discussed can be achieved independently in various examples or may be combined in yet other examples further details of which can be seen with reference to the following description and drawings.

BRIEF DESCRIPTION OF THE DRAWINGS

FIG. 8 shows a flowchart of a method, according to an example implementation;

Figure 1:
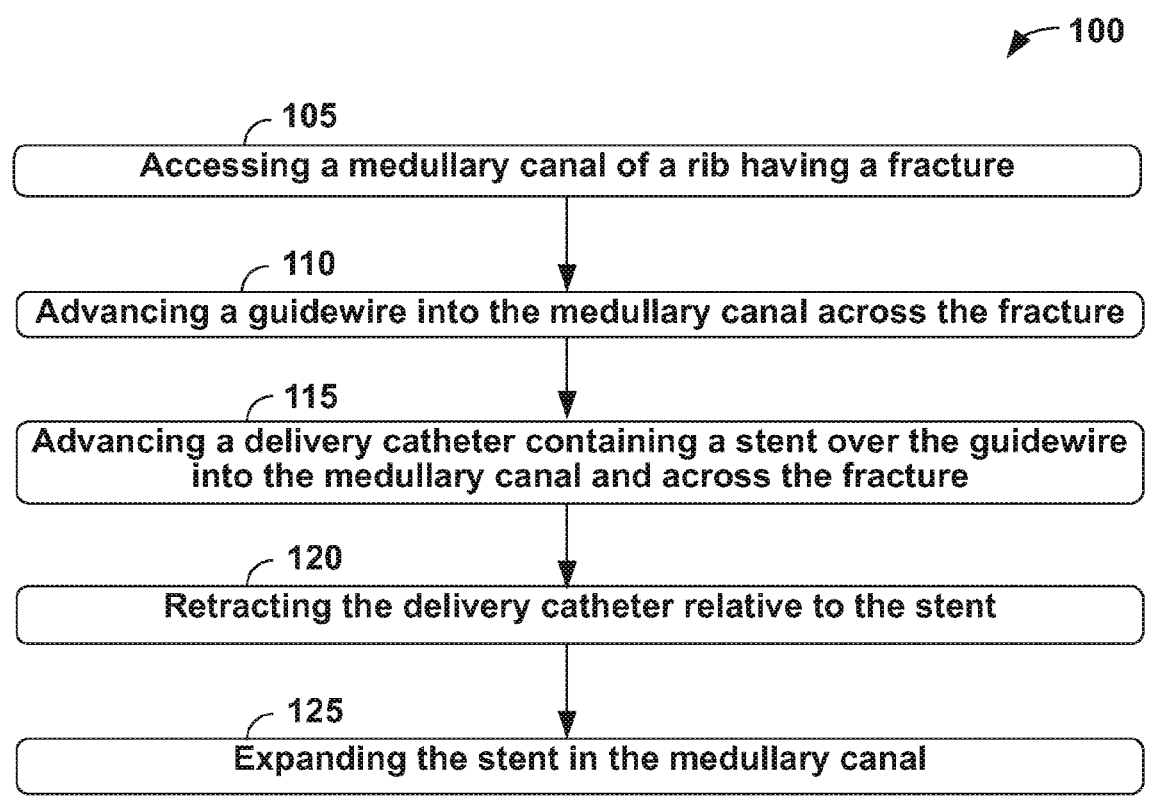
FIG. 1 shows a flowchart of a method, according to an example implementation.
Figure 2:
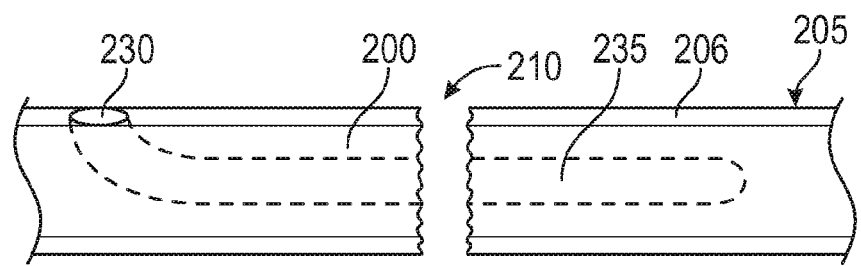
FIG. 2 shows a side cross-sectional view of a rib according to one aspect of the method of FIG. 1.
Figure 3:
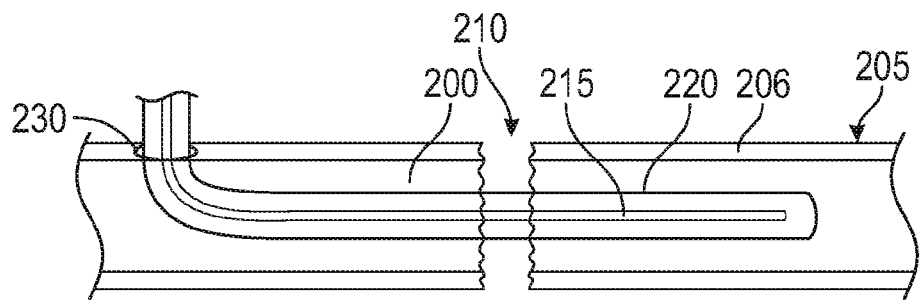
FIG. 3 shows a side cross-sectional view of a rib according to one aspect of the method of FIG. 1.
Figure 4:
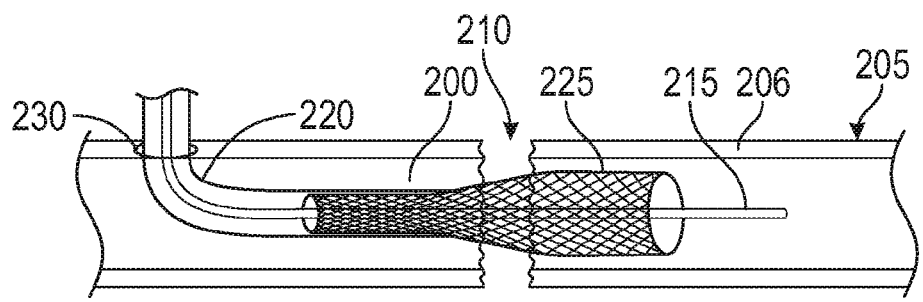
FIG. 4 shows a side cross-sectional view of a rib according to one aspect of the method of FIG. 1.

The drawings are for the purpose of illustrating examples, but it is understood that the inventions are not limited to the arrangements and instrumentalities shown in the drawings.

DETAILED DESCRIPTION

Embodiments of the methods, systems, and apparatus described herein can be used minimally invasive solutions to treat rib fracture. The disclosed example methods, systems, and apparatus may advantageously re-align a fracture to substantially re-establish a rib to a pre-fracture position and/or to provide intra- and/or extra-medullary support. In addition, rib fractures occurring under the scapula may be accessed via an access hole in the rib located a distance away from the scapula without having to move the scapula. Alternatively, the access hole may be located a distance away from a vertebral fracture, not previously accessible under currently known techniques. This technique may be used to treat other fractures not easily accessible or manipulated by known techniques.

The disclosed methods, systems, and apparatus are contemplated to treat single linear fractures and may be effective for non-comminuted fractures involving multiple pieces in some circumstances. For example, situations may arise in which a rib is fractured in two locations such that there is a free-floating segment. In such a case, a stent, a tension line or a polymer, as described in detail below, may span multiple fractures in a rib that is not shattered or comminuted. Once the stent, tension line or polymer are delivered, these supports may act as an internal brace or cast providing structural support while bone heals around it. In certain embodiments, these supports may be left in the bone into perpetuity or may be bio-absorbable.

For example, when a rib is fractured, incisions are made through the skin and one or more access holes are made through stable bone on at least one side of the fractured rib. In an optional embodiment, through-access channels may be created via compression, flushing or reaming of the contents of the medullary canal to create a passageway through the stable bone of the rib to the fracture site and ultimately across the fracture site via one or more of the first and second access holes. Alternatively, the contents of the medullary canal may yield in response to placement of a stent or injection of a polymer. The first and second access holes may be created through a cortex of a rib to a medullary canal of the rib via drilling or using a tapered rod to puncture through the bone. A drill or tapered rod may likewise be used to compress, flush or ream one or more of the marrow or the bone.

In various embodiments described below, percutaneous instruments may be used that screw into a rib to manipulate the rib percutaneously to reduce the fracture site (e.g., where ribs are displaced or offset resulting in overlapping between the rib segments) by moving ribs back into place. For example, a rib may be screwed into or grasped at both ends via other access sites and then held or fixed in place during procedure. In one example, a feedback mechanism may be provided for a tension line to confirm a desired tension has been applied (e.g., a lock rod may be placed at one end and tension may be applied at the other end until there is no further movement of the rod). In addition, fluoroscopy guidance and palpating may also inform proper alignment. And if the access hole to the medullary canal is close enough to the fracture location, this may also help determine alignment.

As used herein, a "guidewire" is an elongated cable comprised of one or more biocompatible materials including metals and polymers. Guidewires may be used for selecting target lumens and guiding catheters to target deployment locations. Guidewires are typically defined as wires used independently of other devices that do not come as part of an assembly.

As used herein, a "stent" is a cylindrical frame or unstructured mesh and refers to any device or structure that adds rigidity, support and/or expansion force to a lumen. The stent can be made of any suitable material, including but not limited to biocompatible metals, implantable quality stainless steel wires, nitinol, cobalt, magnesium, nickel, titanium and alloys thereof, and biocompatible plastics. In addition, the stent structure may include coiled, mesh, zig zag, braided, knitted or woven wires. The stent structure could also include a laser cut sheet or a laser cut tube that may have various lengths, diameters or wall thickness. Alternatively, the stent may include injection molded metal. In another embodiment, the stent may include a bio-absorbable polysaccharide scaffold mesh that may be wrapped or coiled around itself to size the stent for a given medullary canal.

As used herein, an "injection catheter" includes a catheter having a plurality of openings at a first end configured to permit bone cement to exit the catheter. The plurality of openings may be arranged along a length of the injection catheter ranging from 2 mm to 300 mm. The injection catheter is configured for over-the-wire advancement in vivo.

As used herein, "medullary canal" refers to the central cavity of bone shafts where red bone marrow and/or yellow bone marrow (i.e., adipose tissue) is stored.

As used herein, "contents of the medullary canal" include, but are not limited to, marrow, bone fragments, blood and tissue.

As used herein, "a paravertebral fracture" refers to a fracture situated or occurring beside or adjacent to the spinal column.

As used herein, a "drill" may include a drill delivered via catheter or an over-the-wire drill delivered over a guidewire.

As used herein, "a cortex" refers to the hard outer layer of a bone that is composed of cortical bone that is denser than cancellous bone.

As used herein, a "through-and-through wire" is configured to provide medullary continuity and through-and-through access between two access holes to realign a rib (or other fractured bone).

As used herein, a "tension line" includes one or more wires configured to bear tension in response to force applied at respective ends of the tension line. In various embodiments, the wires of the tension line may be braided or helically wound, for example. In embodiments that include the alternating plurality of rods and beads, the rods and beads may be disposed over-the-wire. In some embodiments, the tension line may also be able to be placed into compression.

As used herein, a "stiffening compound" includes bone cement.

Referring now to FIG. 1, a method 100 is illustrated using the elements shown in FIGS. 2-7. Method 100 includes, at block 105, accessing a medullary canal 200 of a rib 205 having a fracture 210. Then, at block 110, a guidewire 215 is advanced into the medullary canal 200 across the fracture 210. Next, at block 115, a delivery catheter 220 containing a stent 225 is advanced over the guidewire 215 into the medullary canal 200 and across the fracture 210. Then, the delivery catheter 220 is retracted relative to the stent 225, at block 120. At block 125, the stent 225 is expanded in the medullary canal 200.

Figure 9:
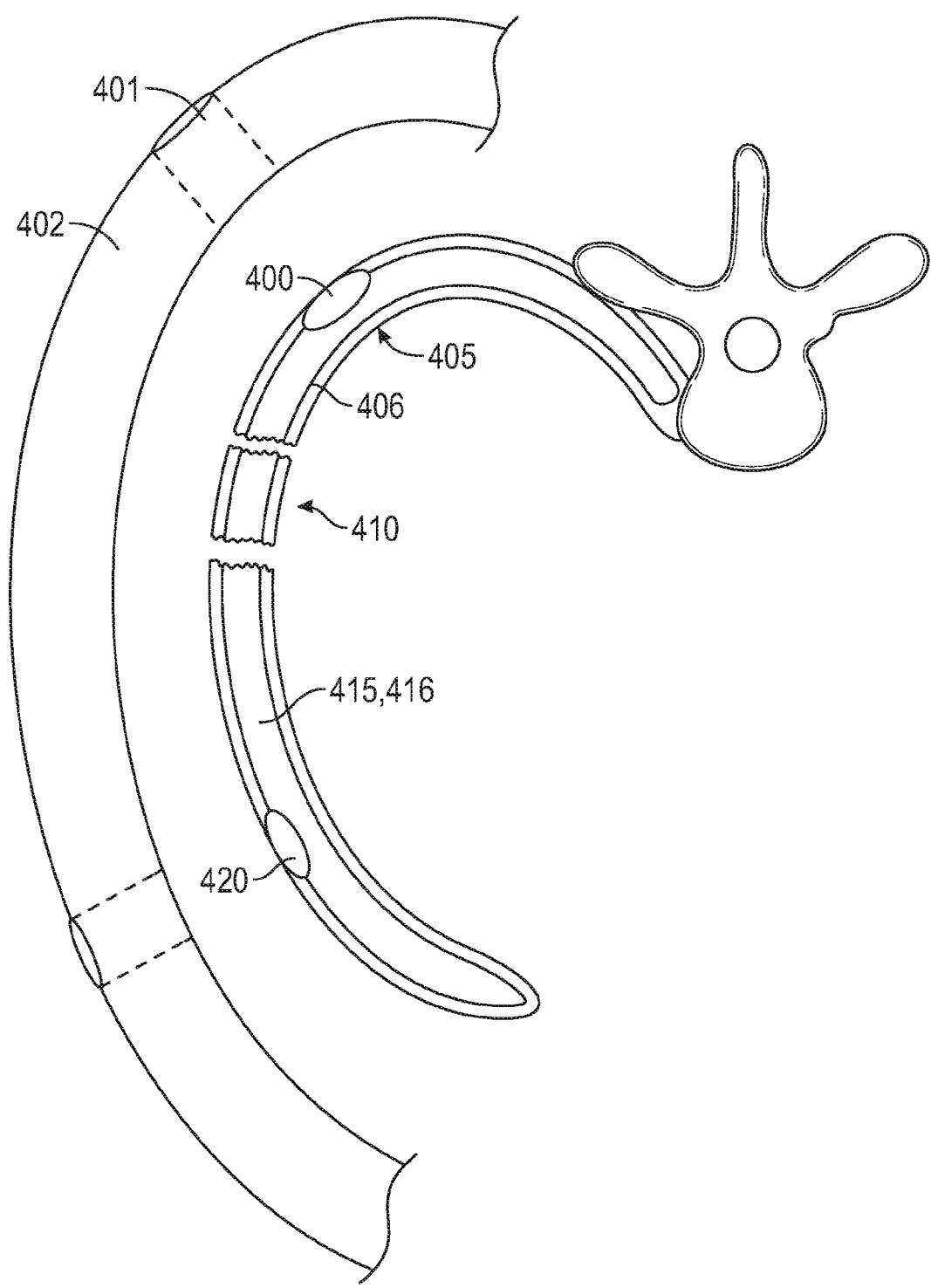
FIG. 9 shows a side cross-sectional view of a rib according to one aspect of the method of FIG. 8.

In one optional embodiment, accessing the medullary canal 200 of the rib 205 having the fracture 210 includes creating an incision 401 in skin 402 of a subject (see, e.g., FIG. 9). Next, blunt dissection down to the rib 205 is performed. And a hole is then drilled through a cortex 206 of the rib 205 on one side of the fracture 210 thereby creating an access hole 230 to the medullary canal 200. In an optional embodiment, the access hole is at least 10 mm from the fracture 210. In another optional embodiment, the access hole 230 is arranged at an acute angle relative to the medullary canal 200, the acute angle ranging from 10 to 70 degrees. In another example embodiment, the access hole 230 is located a distance away from the fracture 210 and the fracture 210 is either located beneath a scapula or the fracture 210 is a paravertebral fracture.

In one optional embodiment, method 100 includes sizing the medullary canal 200 by displacing contents 235 of the medullary canal 200 such that the medullary canal 200 has a diameter of at least 3 mm. In a further embodiment, sizing the medullary canal 200 by displacing the contents 235 of the medullary canal 200 includes one or more of compressing, flushing or reaming one or more of the marrow or the bone.

Figure 10:
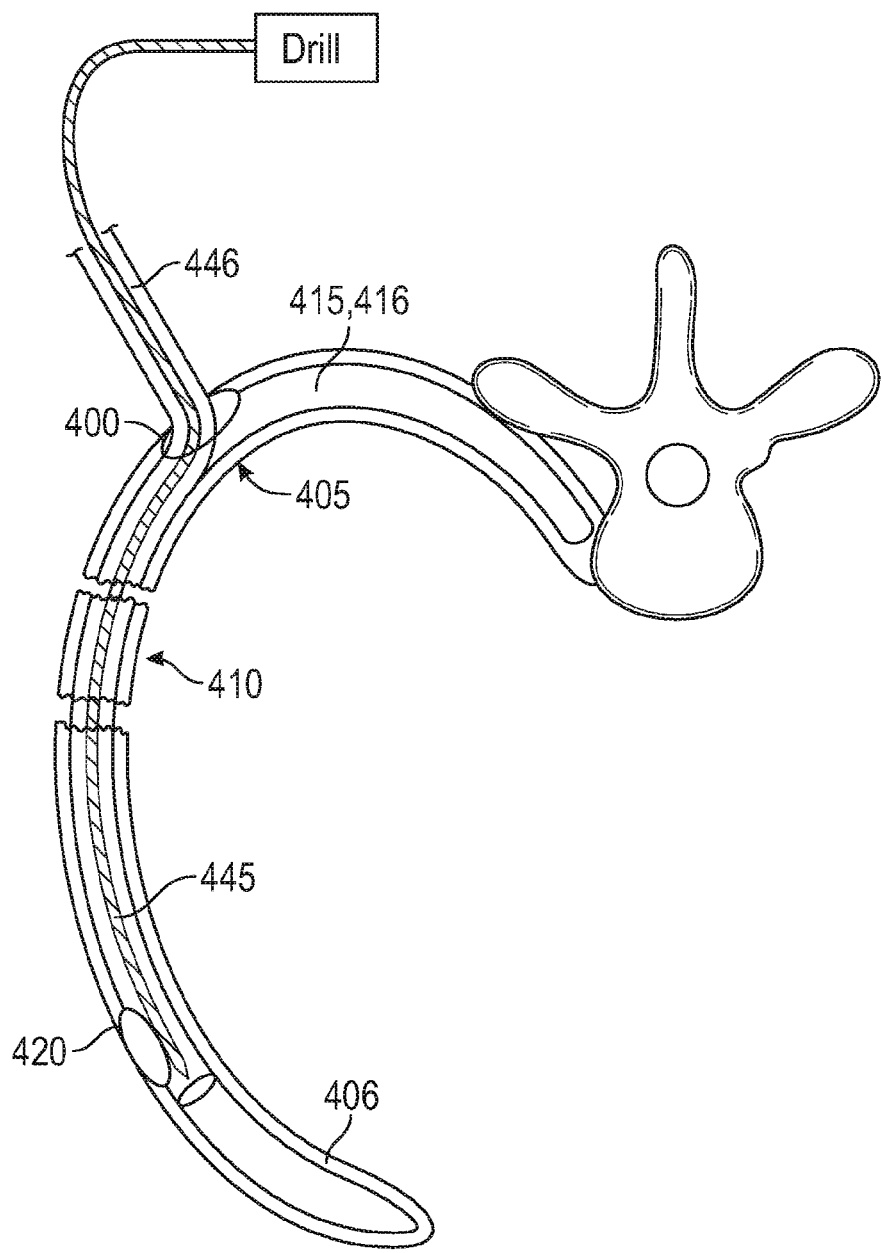
FIG. 10 shows a side cross-sectional view of a rib according to one aspect of the method of FIG. 8.
Figure 11:
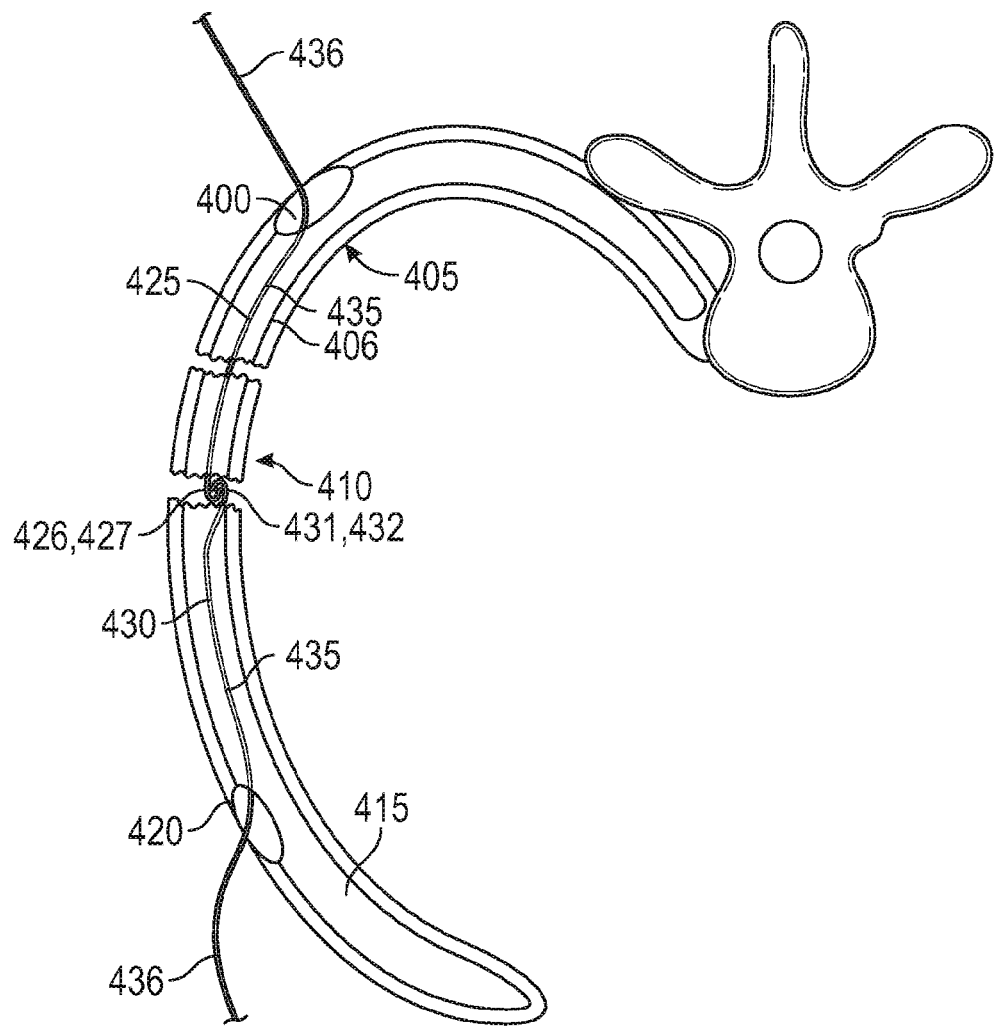
FIG. 11 shows a side cross-sectional view of a rib according to one aspect of the method of FIG. 8.

In an alternative embodiment, sizing the medullary canal 200 by displacing the contents 235 of the medullary canal 200 includes advancing a catheter containing a drill bit through the access hole 230 to the medullary canal 200 (see, e.g., FIG. 10). Then, the drill bit is advanced out of a first end of the catheter. Next, the drill bit is activated thereby causing the drill bit to rotate. And the contents 235 from the medullary canal 200 are advanced into the catheter via the rotating drill bit. The drill bit is then retracted into the catheter and the drill bit and the contents 235 from the medullary canal 200 are advanced out of an access port at the second end of the catheter. In a further optional embodiment, method 100 includes advancing the catheter containing the drill bit through the access hole 230 to the medullary canal 200 includes at least one of using fluoroscopy to visualize the catheter containing the drill bit or palpating the rib 205 and a surrounding tissue.

In another optional embodiment, the method 100 includes leaving the catheter in place in the medullary canal 200 after retraction of the drill bit. In a further embodiment, advancing the guidewire 215 into the medullary canal across the fracture includes advancing the guidewire 215 through the catheter in the medullary canal after retraction of the drill bit. And a further optional embodiment includes removing the catheter from the medullary canal 200 after advancing the guidewire 215 into the medullary canal 200 across the fracture 210.

Figure 5:
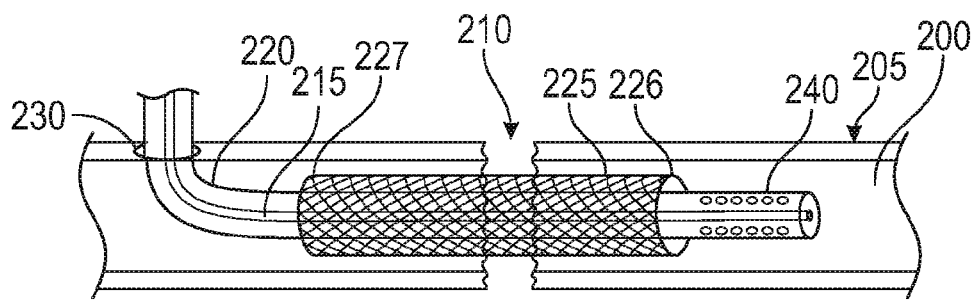
FIG. 5 shows a side cross-sectional view of a rib according to one aspect of the method of FIG. 1.

In one optional embodiment, as shown in FIG. 5, method 100 includes advancing an injection catheter 240 over the guidewire 215 into the medullary canal 200 and across the fracture 200. The medullary canal 200 is then injected with a stiffening compound or a polymer via the injection catheter 240. In a further optional embodiment, the stent 225 has a lumen and the method includes advancing the injection catheter 240 into the lumen of the stent 225 to an end 226 of the stent 225 that is distal to the fracture 210. Then, the injection catheter 240 is retracted through the lumen of the stent 225 while injecting the medullary canal 200 with the stiffening compound or the polymer. In an alternative embodiment, the stent includes an unstructured mesh, and method 100 includes advancing the injection catheter 240 to a proximal end 227 of the stent 225 in the medullary canal 200. Then, the medullary canal 200 is injected with the stiffening compound or the polymer at the proximal end 227 of the stent 225 via the injection catheter 240. In a further embodiment, method 100 includes retracting the injection catheter 240 and the guidewire 215 from the medullary canal 200.

In one optional embodiment, method 100 includes manipulating the rib 205 to realign the medullary canal 200 across the fracture 210.

In one optional embodiment, the stent 225 has a length ranging from 20 mm to 400 mm. In another optional embodiment, the stent 225 is permanent or bio-absorbable. In an alternative embodiment, the stent 225 includes magnesium, a metal, a metal alloy, or a polysaccharide. In a further example embodiment, the stent 225 includes a bio-absorbable polysaccharide scaffold mesh. In still another embodiment, the stent 225 is either balloon expandable or self-expanding.

Figure 6:
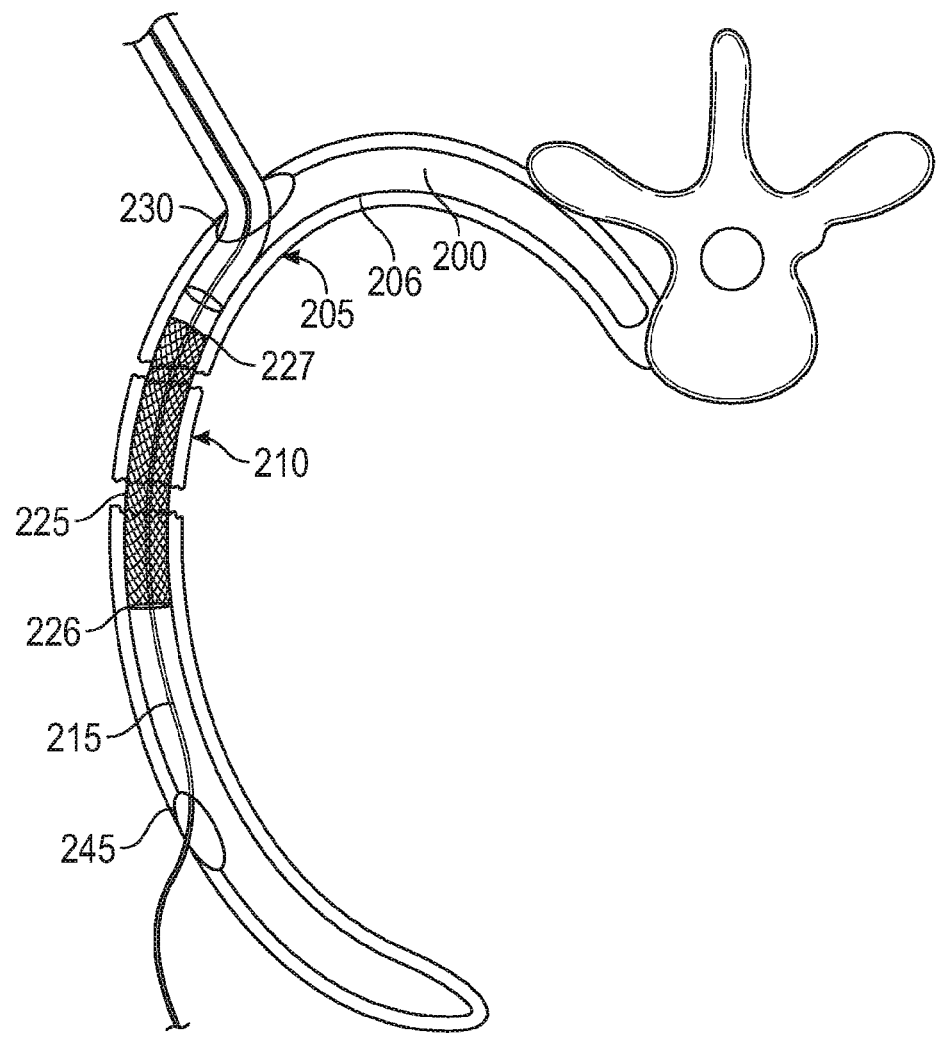
FIG. 6 shows a side cross-sectional view of a rib according to one aspect of the method of FIG. 1.
Figure 7:
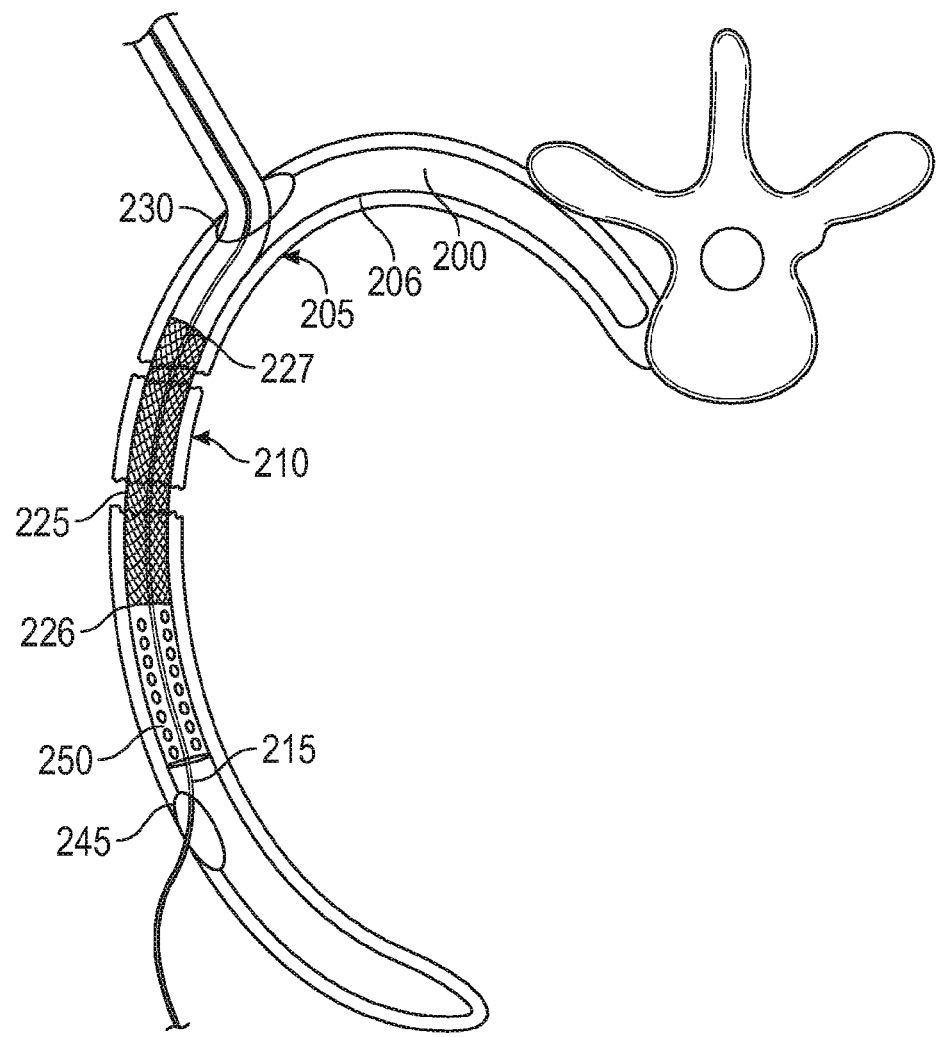
FIG. 7 shows a side cross-sectional view of a rib according to one aspect of the method of FIG. 1.

In another optional embodiment, shown in FIGS. 6-7, a second access hole 245 is created through the cortex 206 of the rib 205 on a second side of the fracture 210. The guidewire 215 is advanced out of the second access hole 245. Then an injection catheter 250 is advanced along the guidewire 215 through a lumen of the stent 225 to a position between the second access hole 245 and a distal end 226 of the stent 225. Bone cement may then be injected into the medullary canal 200 as the injection catheter 250 is retracted out of the medullary canal 200 through the first access hole 230, injecting bone cement in the lumen of the stent 225 and between the proximal end 227 of the stent and the first access hole 230.

Figure 12:
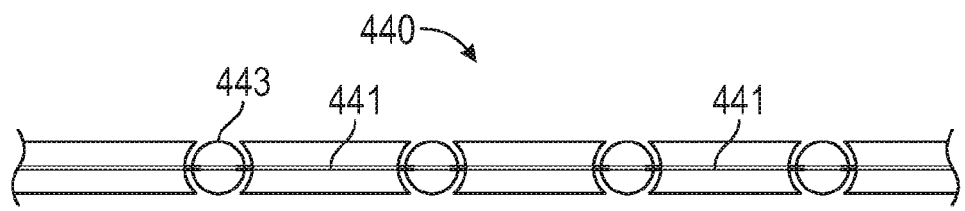
FIG. 12 shows a side view of a tension line according to one aspect of the method of FIG. 8.
Figure 13:
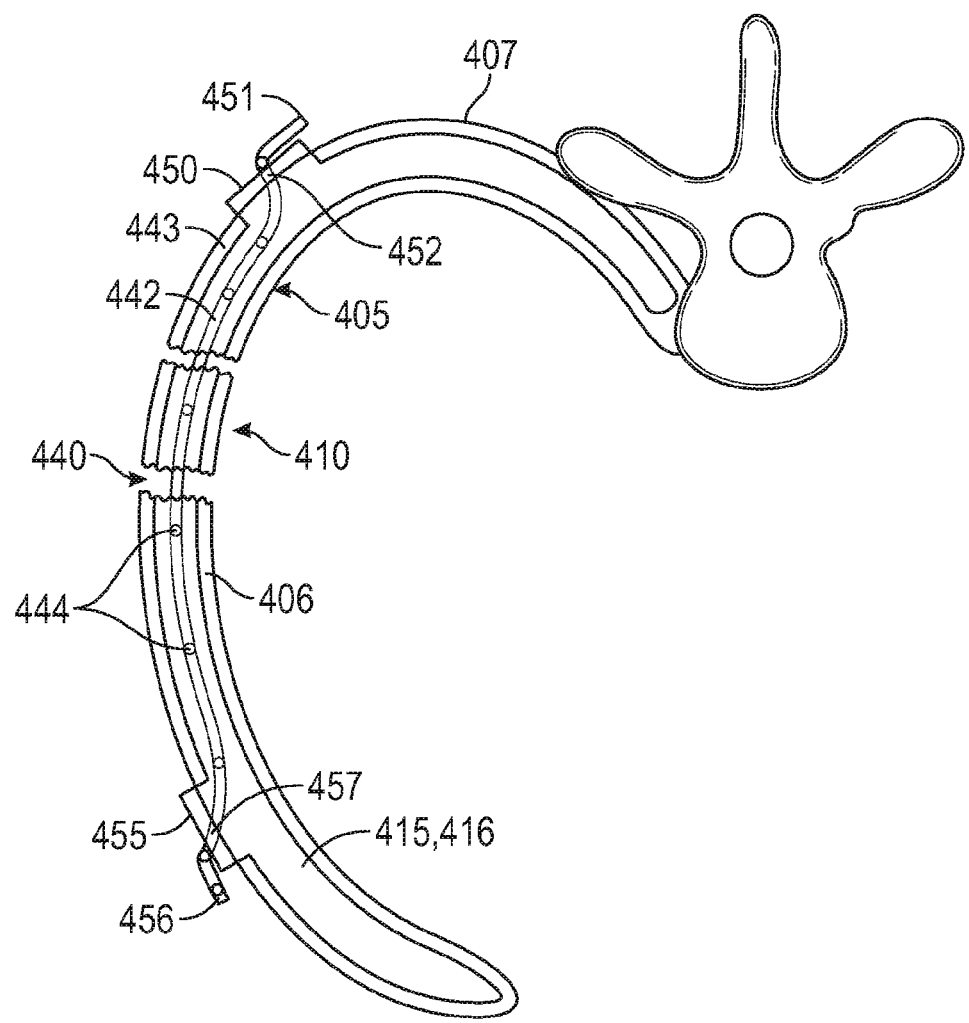
FIG. 13 shows a side cross-sectional view of a rib and a tension line according to one aspect of the method of FIG. 8.

Referring now to FIG. 8, a method 300 is illustrated using the elements shown in FIGS. 9-13. Method 300 includes, at block 305, creating a first access hole 400 through a cortex 406 of a rib 405 on a first side of a fracture 410 to a medullary canal 415 of the rib 405. Then, at block 310, a second access hole 420 is created through the cortex 406 of the rib 405 on a second side of the fracture 410 to the medullary canal 415. Next, at block 315, the medullary canal 415 is accessed through the first access hole 400, via a first wire 425 having a first reciprocal coupling 426 at a free end 427 of the first wire 425. And, at block 320, the medullary canal 415 is accessed through the second access hole 420, via a second wire 430 having second reciprocal coupling 431 at a free end 432 of the second wire 430. Then, at block 325, the free end 427 of the first wire 425 and the free end 432 of the second wire 430 are advanced through the medullary canal 415 until the first reciprocal coupling 426 and the second reciprocal coupling 431 engage with each other thereby providing a through-and-through wire 435. In one optional embodiment, the first reciprocal coupling 426 and the second reciprocal coupling 431 comprise a pair of magnets, a pair of hooks, or a hook and a snare. A tension line 440 is then advanced through the first access hole 400 into the medullary canal 415 across the fracture 410 and out the second access hole 420, at block 330. As shown in FIG. 12, the tension line 440 includes a wire 441 disposed through an alternating plurality of rods 442 and beads 443 arranged in series along at least a portion of the length of the tension line 440. And method 100 includes, at block 335, placing the tension line 440 under tension.

In one optional embodiment, a first end 449 of the tension line 440 is coupled to an end 436 of the through-and-through wire 435. In this embodiment, advancing the tension line 440 through the first access hole 400 into the medullary canal 415 across the fracture 410 and out the second access hole 420 includes advancing the through-and-through wire 435 out of the medullary canal 415 via one of the first access hole 400 or the second access hole 420 and thereby pulling the tension line 440 through the medullary canal 415. In a further optional embodiment, method 300 includes uncoupling the tension line 440 from the through-and-through wire 435.

In another optional embodiment, method 300 includes advancing a delivery sleeve over the through-and-through wire 435 through the first access hole 400 into the medullary canal 415 across the fracture 410 and out the second access hole 420. Then, the through-and-through wire 435 is removed from the medullary canal 415. In this embodiment, advancing the tension line 440 through the first access hole 400 into the medullary canal 415 across the fracture 410 and out the second access hole 420 includes at least one of pushing and pulling the tension line 440 into a first end of the delivery sleeve until the tension line 440 advances out of a second end of the delivery sleeve. Then, the delivery sleeve is removed from the medullary canal 415 such that the tension line 440 remains in the medullary canal 415.

In one optional embodiment, method 300 includes sizing the medullary canal by displacing contents 416 of the medullary canal 415 such that the medullary canal 415 has a diameter of at least 2 mm. In a further embodiment, sizing the medullary canal 415 by displacing the contents 416 of the medullary canal 415 includes one or more of compressing, flushing or reaming one or more of the marrow or the bone.

In an alternative embodiment, shown in FIG. 10, sizing the medullary canal 415 by displacing the contents 416 of the medullary canal 415 includes advancing a flexible drill bit 445 over the through-and-through wire 435 into the medullary canal 415. Then, the flexible drill bit 445 is activated thereby causing the flexible drill bit 445 to rotate. And the flexible drill bit 445 is removed from the medullary canal 415. In one embodiment, the flexible drill bit is delivered to the medullary canal 415 via a delivery catheter 446.

In one optional embodiment, method 300 further includes advancing a first anchoring hub 450 over a first end 451 of the tension line 440 down to the cortex 406 of the rib 405 surrounding the first access hole 400 and advancing a second anchoring hub 455 over a second end 456 of the tension line 435 down to the cortex 406 of the rib 405 surrounding the second access hole 420. In this embodiment, a through-hole 452 in the first anchoring hub 450 has a diameter smaller than at least one of the alternating plurality of rods 442 and beads 443, and a through-hole 457 in the second anchoring hub 455 has a diameter smaller than at least one of the alternating plurality of rods 442 and beads 443. In a further embodiment, method 300 includes transferring tension from the tension line 440 to an outer cortex 407 of the rib 405 via the first anchoring hub 450 and the second anchoring hub 455.

In one optional embodiment, method 300 includes applying a bone cement within the first access hole 400 and the second access hole 420 and surrounding the first end 451 and the second end 456 of the tension line 440. In a further embodiment, applying the bone cement within the first access hole 400 and the second access hole 420 and surrounding the first end 451 and the second end 456 of the tension line 440 includes injecting the bone cement into one or more of the first access hole 400 and the second access hole 420 and the medullary canal 415 via syringe.

In another optional embodiment, method 300 includes bending the tension line 440 at one or more joints 444 between the alternating plurality of the rods 442 and beads 443 to conform to a native configuration of the rib 405, while advancing the tension line 440 through the first access hole 400 into the medullary canal 415 across the fracture 410 and out the second access hole 420.

In a further optional embodiment, method 300 includes anchoring the second end 456 of the tension line 440 to the cortex 406 of the bone 405 at the second access hole 420. Then, the tension line 440 is cut adjacent to the first access hole 400. And the first end 451 of the tension line 440 is anchored to the cortex 406 of the bone 405 at the first access hole 400.

In an example embodiment, the alternating plurality of rods 442 and beads 443 form a support for the rib 405, when the tension line 440 is placed under tension. In a further embodiment, placing the tension line 440 under tension creates a bending force. In still another embodiment, placing the tension line 440 under tension creates a lateral fixation and an axial fixation within the rib 405.

In an optional embodiment, the alternating plurality of rods 442 and beads 443 include magnesium, titanium, nitinol, stainless steel or combinations thereof. In another example embodiment, the plurality of rods 442 have a length ranging from 2 mm to 35 mm and a diameter ranging from 2 mm to 10 mm, and the plurality of beads 443 have a diameter ranging from 2 mm to 10 mm.

In one optional embodiment, the first access hole and the second access hole are at least 10 mm from the fracture. In another example embodiment, the first access hole 400 and the second access hole 420 are arranged at an acute angle relative to the medullary canal 415, the acute angle ranging from 10 to 70 degrees.

In one optional embodiment, the method 300 includes manipulating the rib to realign the medullary canal across the fracture.

Figure 14:
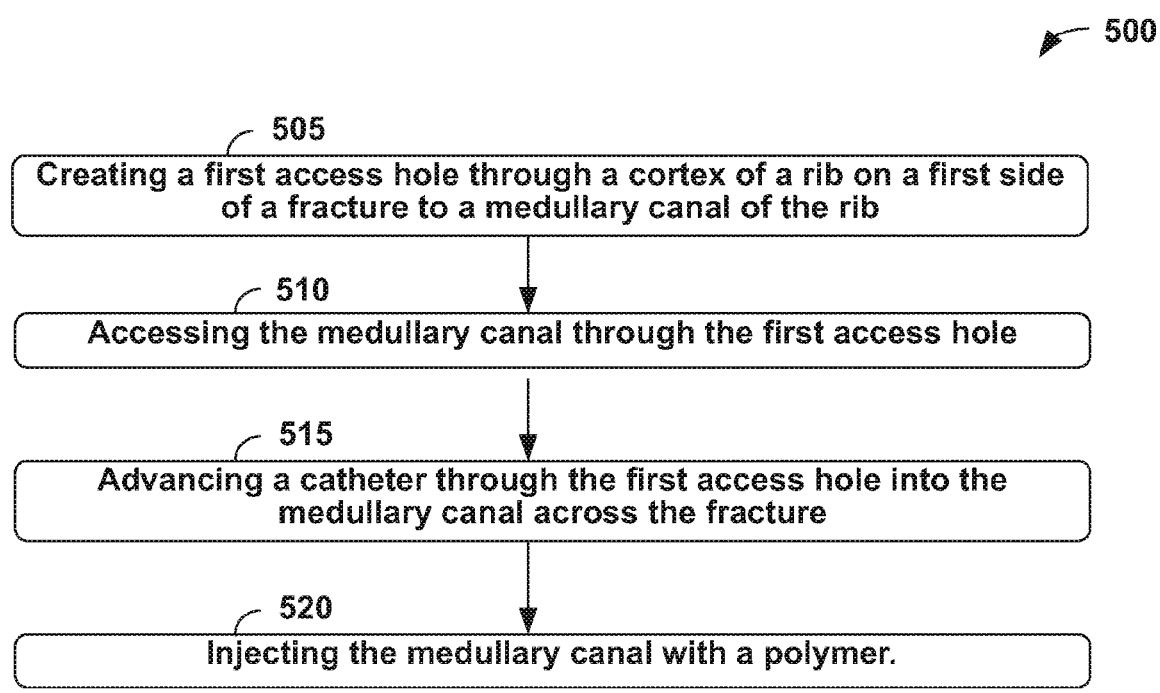
FIG. 14 shows a flowchart of a method, according to an example implementation.

Referring now to FIG. 14, a method 500 is illustrated using various elements shown in FIGS. 6-7. Method 500 includes, at block 505, creating a first access hole 230 through a cortex 206 of a rib 205 on a first side of a fracture 210 to a medullary canal 200 of the rib. Then, at block 510, the medullary canal 200 is accessed through the first access hole 230. Next, at block 515, a catheter 250 advanced through the first access hole 230 into the medullary canal 200 across the fracture 210. And then injecting the medullary canal 200 with a polymer, at block 220.

In one optional embodiment, the method 500 includes sizing the medullary canal 200 by displacing contents of the medullary canal 200 such that the medullary canal 200 has a diameter of at least 2 mm. In a further embodiment, sizing the medullary canal 200 by displacing the contents 235 of the medullary canal 200 includes one or more of compressing, flushing or reaming one or more of the marrow or the bone.

In another embodiment, method 500 includes retracting the catheter through the medullary canal 200 while injecting the medullary canal 200 with the polymer.

In a still another optional embodiment, method 500 includes creating a second access hole 245 through the cortex 206 of the rib 205 on a second side of the fracture 210 to the medullary canal 200 of the rib 205. And injecting the medullary canal 200 with the polymer until the polymer exits the medullary canal 200 through the second access hole 245. In a further optional embodiment, after the polymer exits the medullary canal 200 through the second access hole 245, the catheter 250 is retracted a distance and continues to inject the medullary canal 200 with the polymer.

In another optional embodiment, method 500 includes injecting the medullary canal 200 with the polymer until a flow resistance of the polymer is detected by an operator. Then, the catheter 250 is retracted through the medullary canal 200 a distance. And injection and retraction steps are repeated until the medullary canal 200 has been filled with the polymer. In still another optional embodiment, method 500 includes expanding the polymer due to exposure to fluid and then curing the polymer and thereby forming a support for the rib 205.

In one optional embodiment, method 500 includes re-establishing the rib 205 in a near native position relative to the fracture 210. In an alternative embodiment, method 500 includes manipulating the rib 205 to realign the medullary canal across the fracture 210.

In one option embodiment, the first access hole is at least 10 mm from the fracture 210. In another example embodiment, the first access hole 230 is arranged at an acute angle relative to the medullary canal 200, the acute angle ranging from 10 to 70 degrees. In another embodiment, the first access hole is located a distance away from the fracture 210 and the fracture 210 is either located beneath a scapula or the fracture is a paravertebral fracture.

Figure 15:
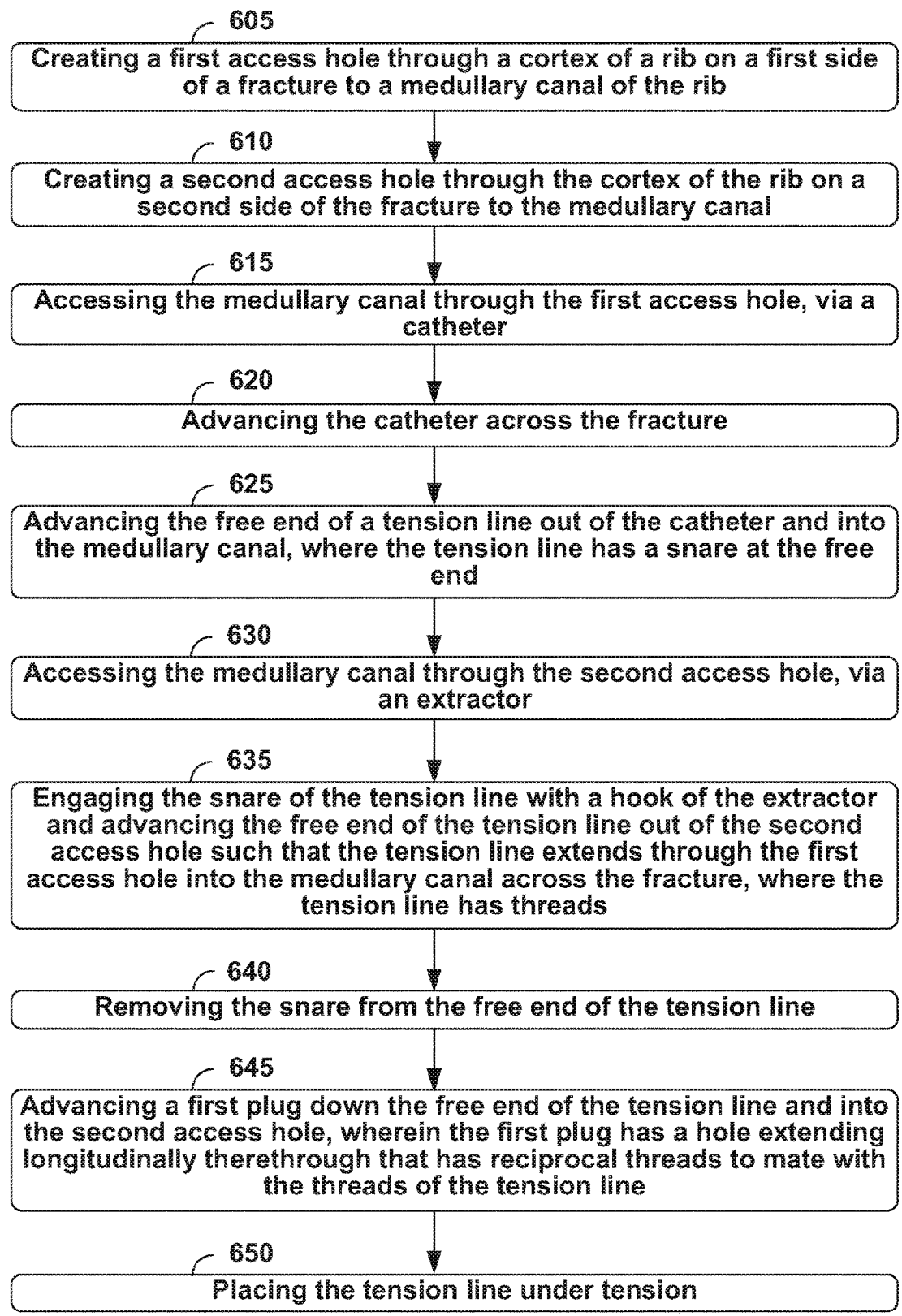
FIG. 15 shows a flowchart of a method, according to an example implementation.

Referring now to FIG. 15, a method 600 is illustrated using various elements shown in FIGS. 16-22. Method 600 includes, at block 605, creating a first access hole 700 through a cortex 706 of a rib 705 on a first side of a fracture 710 to a medullary canal 715 of the rib 705. Then, at block 610, a second access hole 720 is created through the cortex 706 of the rib 705 on a second side of the fracture 710 to the medullary canal 715. Next, at block 615, the medullary canal 715 is accessed through the first access hole 700, via a catheter 725. The catheter 725 is then advanced across the fracture 710, at block 620. A free end 731 of a tension line 730 is next advanced out of the catheter 725 and into the medullary canal 715, at block 625, where the tension line 730 has a snare 732 at the free end 731. The medullary canal 715 is then accessed through the second access hole 720, via an extractor 735, at block 630. And the snare 732 of the tension line 730 is engaged with a hook 736 of the extractor 735 and the free end 731 of the tension line 730 is advanced out of the second access hole 720 such that the tension line 730 extends through the first access hole 700 into the medullary canal 715 across the fracture 710, at block 635, where the tension line 730 has threads 733. Then, at block 640, the snare 732 is removed from the free end 731 of the tension line 730. At block 645, a first plug 740 is advanced down the free end 731 of the tension line 730 and into the second access hole 720, where the first plug 740 has a hole 741 extending longitudinally therethrough that has reciprocal threads to mate with the threads 733 of the tension line 730. And the tension line 730 is then placed under tension, at block 650.

In one optional embodiment, the first access hole 700 has a diameter of at least 1 cm and the second access hole 720 has a diameter of 5 mm to 10 mm. In another example embodiment, the first access hole 700 is arranged at an acute angle relative to the medullary canal 715, the acute angle ranging from 10 to 70 degrees and where the second access hole 720 is arranged at an angle relative to the medullary canal 715 ranging from 10 to 90 degrees.

In another optional embodiment, an extramedullary side 742 of the first plug 740 has a diameter ranging from 6 mm to 8 mm and an intramedullary side 743 of the first plug 740 has a diameter ranging from about 4 mm to 5 mm. In a further example embodiment, walls 744 extending between the extramedullary side 742 and the intramedullary side 743 of the first plug 740 are concave.

In one optional embodiment, advancing the first plug 740 down the free end 731 of the tension line 730 and into the second access hole 720 includes rotating the first plug 740 about the tension line 730 and screwing the first plug 740 into the bone defining the second access hole 720.

In one optional embodiment, the tension line 730 has a diameter ranging from 1 mm to 10 mm.

In one optional embodiment, the method 600 includes advancing a plurality of stents 745 over the tension line 730 through the first access hole 700 into the medullary canal 715 until a length of the medullary canal 715 between the first access hole 700 and the second access hole 720 is filled with the plurality of stents 745. In a further optional embodiment, each of the plurality of stents 745 has a concave face at a first end 746 and a convex face at a second end 747 such that, when the plurality of stents 745 are arranged adjacent to each other along the tension line 730, the concave face of the first end 746 of a first stent 750 will mate with the convex face of the second end 747 of an adjacent second stent 751.

In another optional embodiment, the plurality of stents 245 each have a circular cross-section and a diameter ranging from 1 mm to 5 mm. In an alternative embodiment, the plurality of stents 245 each have an oval cross-section with a minor axis ranging from 2 mm to 5 mm and a major axis ranging from 3 mm to 8 mm. In a further example embodiment, the plurality of stents 245 each have a length ranging from 3 mm to 10 mm. In one optional embodiment, the second plug 755 has an extramedullary side 757 that is flat and an intramedullary side 758 that is convex.

In one optional embodiment, method 600 includes advancing a second plug 755 down an end of the tension wire 730 extending out of the first access hole 700 and into the first access hole 700, where the second plug 755 has a hole 756 extending longitudinally therethrough that has reciprocal threads to mate with the threads of the tension line 730. In a further optional embodiment, advancing the second plug 755 down the end of the tension wire 730 extending out of the first access hole 700 and into the first access hole 700 includes rotating the second plug 755 about the tension wire 730 and screwing the second plug 755 into the bone defining the first access hole 700.

In a further optional embodiment, method 600 includes injecting the medullary canal with a stiffening compound or a polymer.

In yet another optional embodiment, method 600 includes sizing the medullary canal 715 by displacing the contents 716 of the medullary canal 715. In a further example, sizing the medullary canal 715 by displacing the contents 716 of the medullary canal 715 includes one or more of compressing, flushing or reaming one or more of the marrow or the bone.

A system, shown in FIGS. 16-22, that is utilized by method 600 includes a tension line 730 having a removable snare 732 at a free end 731, where the tension line 730 has threads. The system also includes a first plug 740 configured to be advanced down the free end 731 of the tension line 730 and a second access hole 720 of a rib 705, where the first plug 740 has a hole 741 extending longitudinally therethrough that has reciprocal threads to mate with the threads of the tension line 730. The system further includes a plurality of stents 245 configured to be advanced over the tension line 730 through a first access hole 700 in the rib 705 into the medullary canal of the rib until a length of the medullary canal 715 between the first access hole 700 and the second access hole 720 is filled with the plurality of stents 745. Each of the plurality of stents 745 has a concave face at a first end 746 and a convex face at a second end 747 such that, when the plurality of stents 745 are arranged adjacent to each other along the tension line 730, the concave face of the first end 746 of a first stent 750 will mate with the convex face of the second end of an adjacent second stent 751. And the system includes a second plug 755 configured to be advanced down an end of the tension wire 730 and into the first access hole 700, where the second plug 755 has a hole 756 extending longitudinally therethrough that has reciprocal threads to mate with the threads of the tension line 730.

In one optional embodiment, an extramedullary side 742 of the first plug 740 has a diameter ranging from 6 mm to 8 mm and an intramedullary side 743 of the first plug 740 has a diameter ranging from about 4 mm to 5 mm. In a further example embodiment, walls 744 extending between the extramedullary side 742 and the intramedullary side 743 of the first plug 740 are concave. In one optional embodiment, the second plug 755 has an extramedullary side 757 that is flat and an intramedullary side 758 that is convex.

In one optional embodiment, the tension line 730 has a diameter ranging from 1 mm to 10 mm.

In one optional embodiment, the plurality of stents 245 each have a circular cross-section and a diameter ranging from 1 mm to 5 mm. In another example embodiment, the plurality of stents 245 each have an oval cross-section with a minor axis ranging from 2 mm to 5 mm and a major axis ranging from 3 mm to 8 mm. In a further example embodiment, the plurality of stents 245 each have a length ranging from 3 mm to 10 mm.

Figure 16:
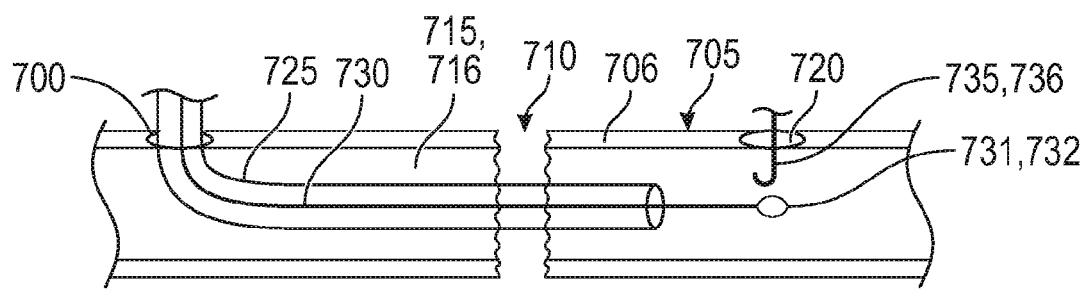
FIG. 16 shows a side cross-sectional view of a rib according to one aspect of the method of FIG. 15.
Figure 17:
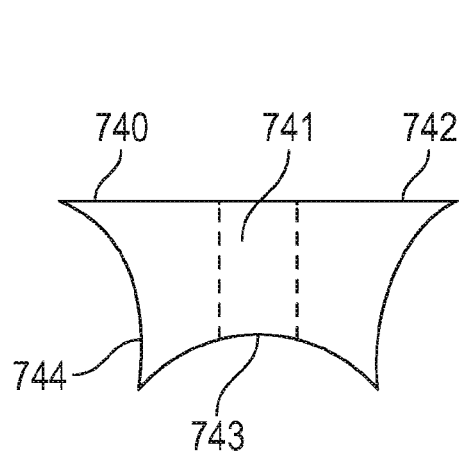
FIG. 17 shows a side view of one embodiment of a first plug according to the example method of FIG. 15.
Figure 18:
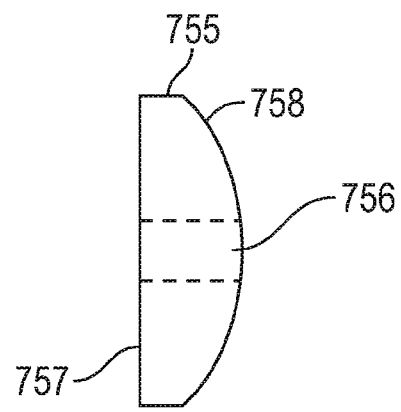
FIG. 18 shows a side view of one embodiment of a second plug according to the example method of FIG. 15.
Figure 19:
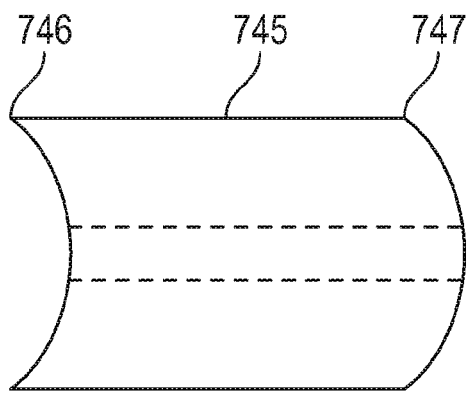
FIG. 19 shows a side view of one embodiment a stent according to the example method of FIG. 15.
Figure 20:
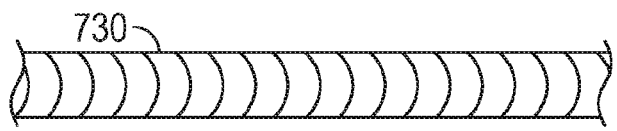
FIG. 20 shows a side view of one embodiment of a guidewire according to the example method of FIG. 15.
Figure 21:
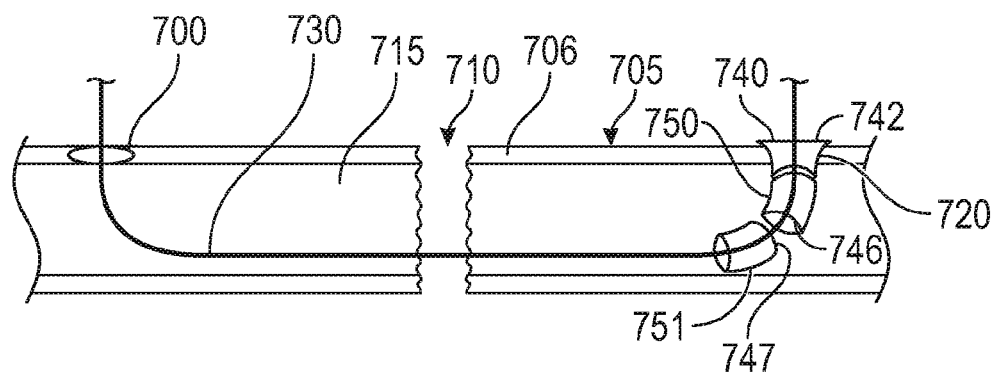
FIG. 21 shows a side cross-sectional view of a rib according to one aspect of the method of FIG. 15.
Figure 22:
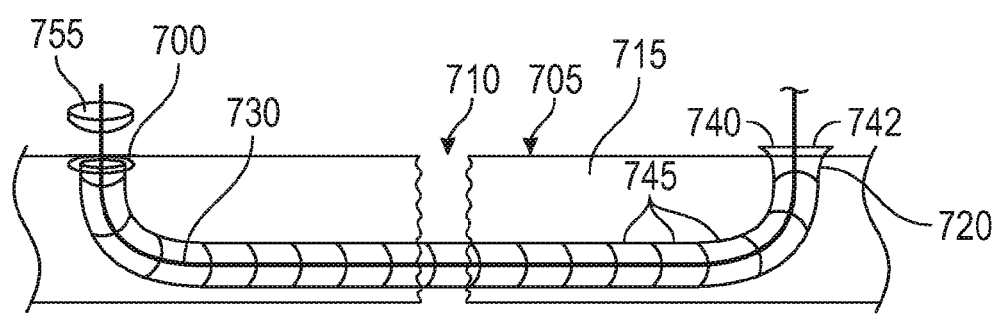
FIG. 22 shows a side cross-sectional view of a rib according to one aspect of the method of FIG. 15.
Figure 23:
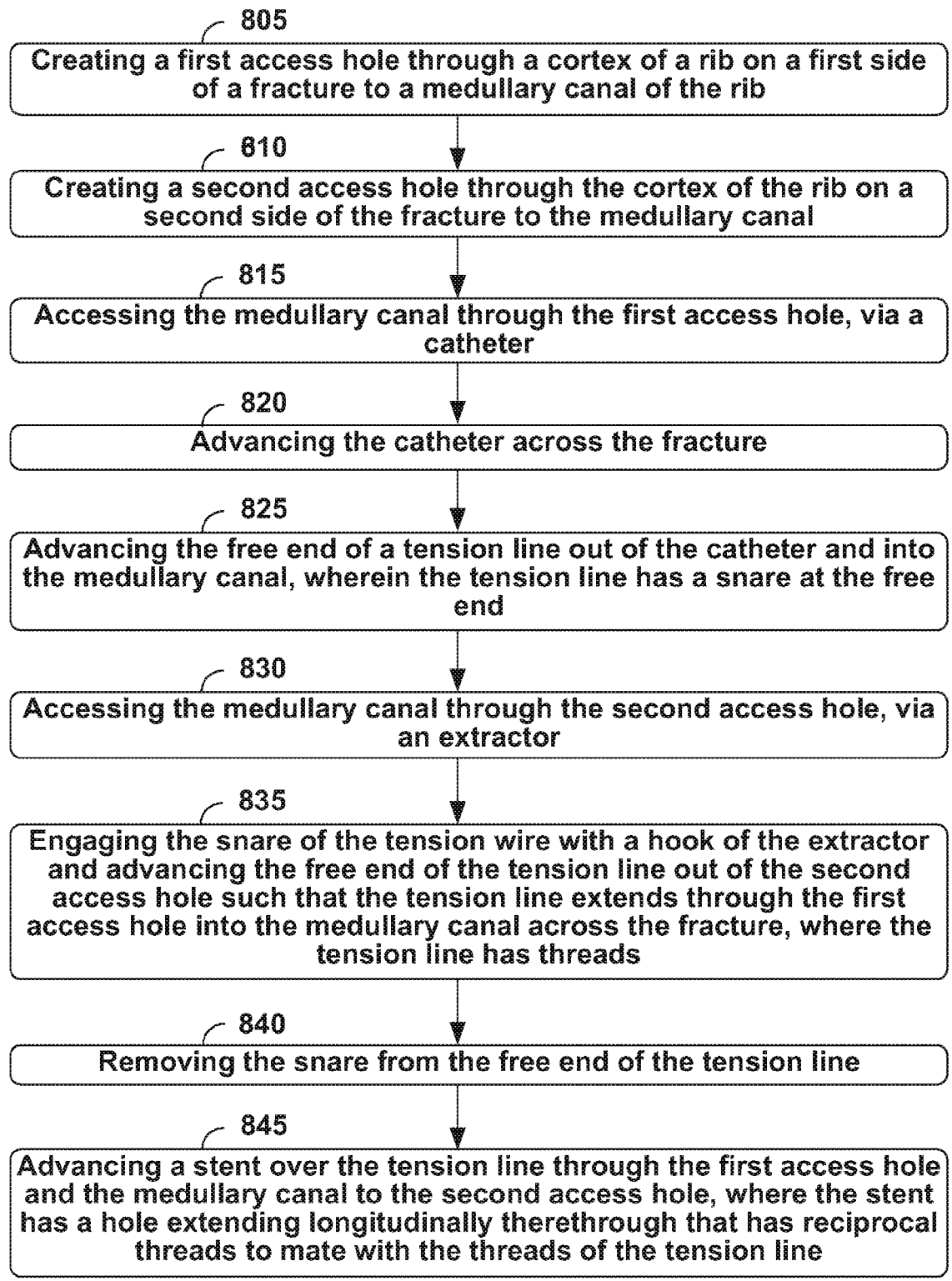
FIG. 23 shows a flowchart of a method, according to an example implementation.
Figure 24:
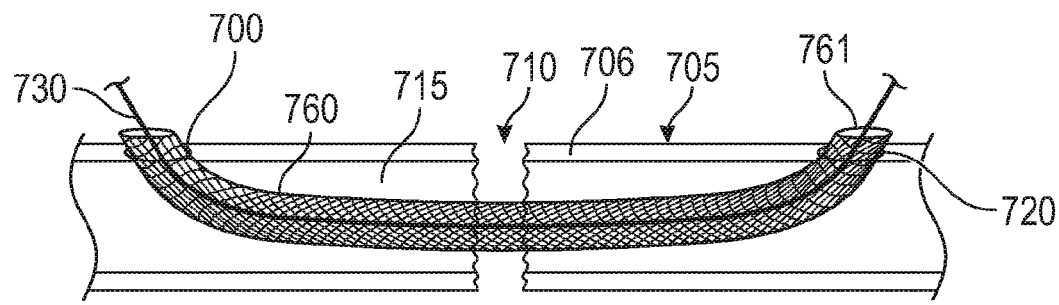
FIG. 24 shows a side cross-sectional view of a rib with a stent deployed therein according to one aspect of the method of FIG. 23.

Referring now to FIG. 23, a method 800 is illustrated using various elements shown in FIGS. 16 and 24. Method 800 includes, at block 805, creating a first access hole 700 through a cortex 706 of a rib 705 on a first side of a fracture to a medullary canal 715 of the rib 705. Next, at block 610, a second access 720 hole is created through the cortex 706 of the rib 705 on a second side of the fracture 710 to the medullary canal 715. Then, at block 615, the medullary canal 715 is accessed through the first access hole 700, via a catheter 725. The catheter 725 is then advanced across the fracture 710, at block 620. The free end 731 of a tension line 730 is then advanced out of the catheter 725 and into the medullary canal 715, where the tension line 730 has a snare 732 at the free end 731, at block 625. Then, at block 630, the medullary canal 715 is accessed through the second access hole 720, via an extractor 735. Next, at block 635, the snare 732 of the tension wire 730 is engaged with a hook 736 of the extractor 735 and advancing the free end 731 of the tension line 730 out of the second access hole 720 such that the tension line 730 extends through the first access hole 700 into the medullary canal 715 across the fracture 710, where the tension line 730 has threads. Then, at block 640, the snare 732 is removed from the free end 731 of the tension line 730. And, at block 645, a stent 760 is advanced over the tension line through the first access hole and the medullary canal to the second access hole, where the stent 760 has a hole extending longitudinally therethrough that has reciprocal threads to mate with the threads of the tension line.

In one optional embodiment, any portion of the stent 760 extending out of either of the first access hole 700 and the second access hole 720 is cut.

In one optional embodiment, method 800 includes injecting the first access hole 700 and the second access hole 720 with a stiffening component or a polymer.

In one optional embodiment, a first end 761 of the stent 760 is tapered.

In one embodiment, method 800 includes sizing the medullary canal 715 by displacing the contents 716 of the medullary canal 715. In one optional embodiment, sizing the medullary canal 715 by displacing the contents 716 of the medullary canal 715 includes one or more of compressing, flushing or reaming one or more of the marrow or the bone.

Figure 25:
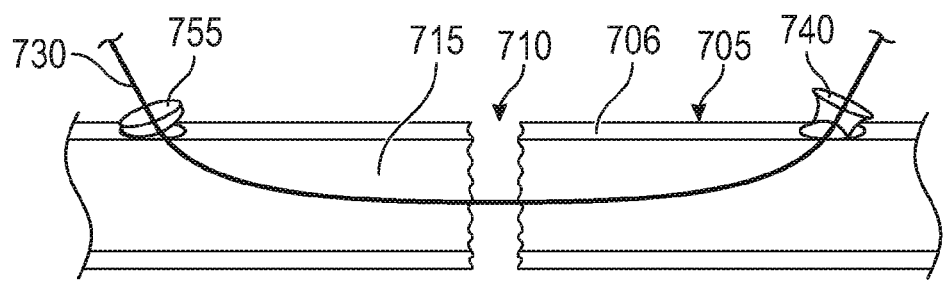
FIG. 25 shows a side cross-sectional view of a rib with a first plug and a second plug deployed therein according to an example implementation.

In FIG. 25, an alternative to stent 760, is to use the first plug 740 and the second plug 755 with tension line 730, but without the plurality of stents 745. The act of screwing the second plug 755 into the second access hole 720 over the threaded tension line 730 exerts a force across the rib that brings the segments of the rib together and into alignment.

Figure 26:
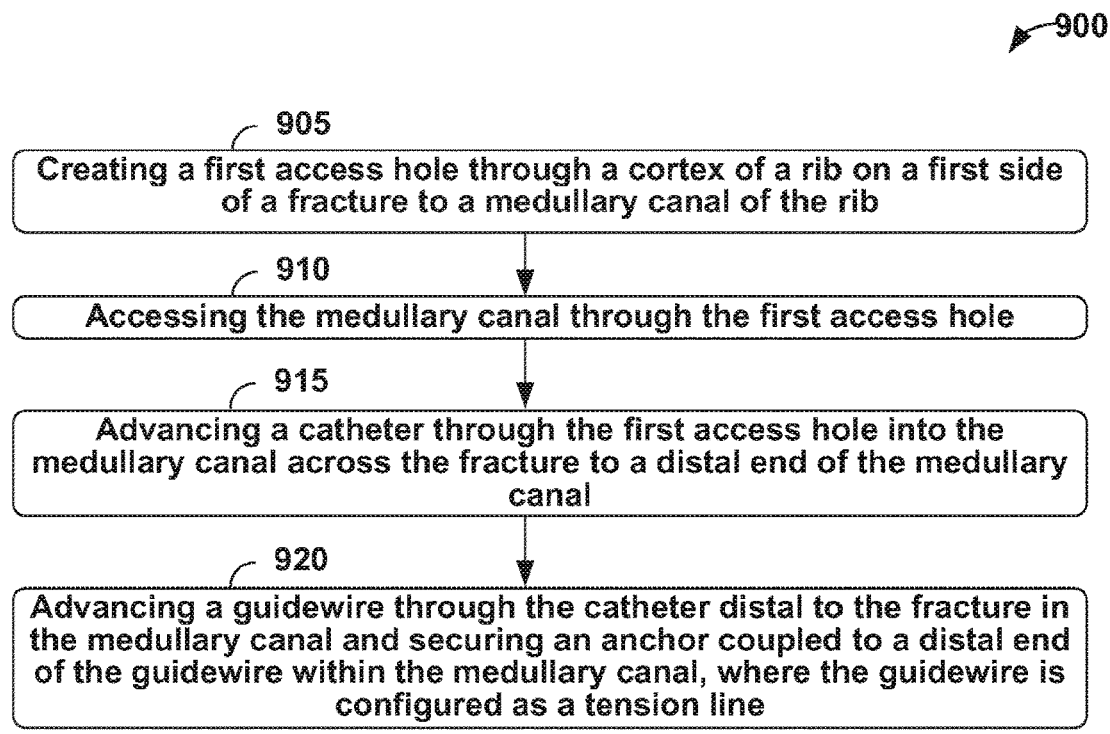
FIG. 26 shows a flowchart of a method, according to an example implementation.
Figure 27:
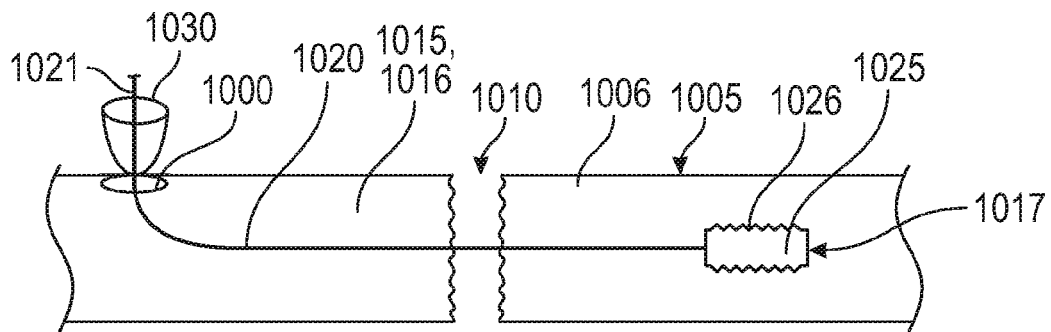
FIG. 27 shows a side cross-sectional view of a rib with an anchor disposed therein according to one aspect of the method of FIG. 26.
Figure 28:
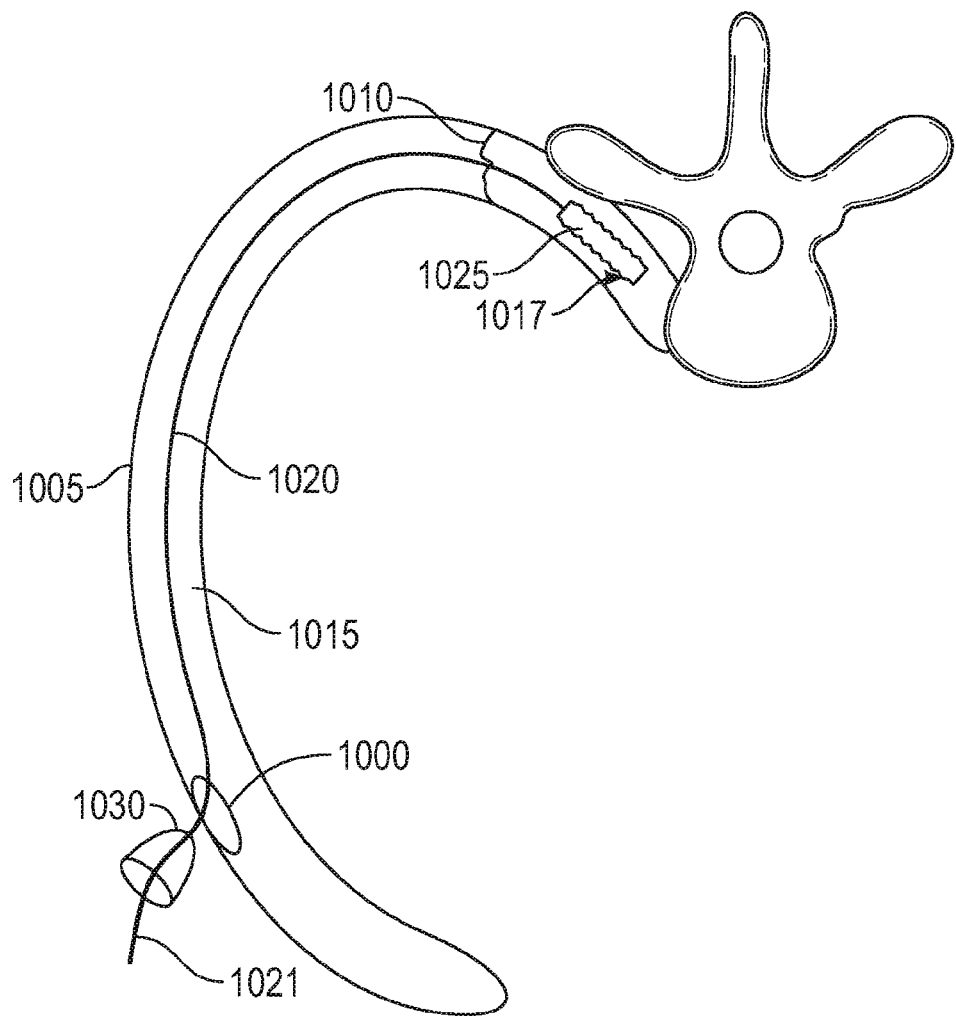
FIG. 28 shows a side cross-sectional view of a rib with an anchor disposed therein according to one aspect of the method of FIG. 26.

Referring now to FIG. 26, a method 900 is illustrated using various elements shown in FIGS. 27-28. Method 900 includes, at block 905, creating a first access hole 1000 through a cortex 1006 of a rib 1005 on a first side of a fracture 1010 to a medullary canal 1015 of the rib 1005. Then, at block 910, the medullary canal 1015 is accessed through the first access hole 1000. Next, at block 915, a catheter is advanced through the first access hole 1000 into the medullary canal 1015 across the fracture 1010 to a distal end 1017 of the medullary canal 1015. And, at block 920, a guidewire 1020 is advanced through the catheter distal to the fracture 1010 in the medullary canal 1015 and an anchor 1025 coupled to a distal end of the guidewire 1020 is secured within the medullary canal 1015, where the guidewire 1020 is configured as a tension line.

In one optional embodiment, method 900 includes injecting the medullary canal 1015 with a polymer distal to the fracture 1010, the polymer configured to secure the anchor 1025 within the medullary canal 1015. In one optional embodiment, an exterior surface 1026 of the anchor 1025 has a plurality of grooves, depressions or pores configured to receive the polymer. In a further optional embodiment, the anchor 1025 is expandable and includes a stent or a plurality of radially extending barbs, where the anchor 1025 is configured to be self-expanding or balloon-expandable. In yet another example embodiment, the anchor 1025 is manually expandable and has a plurality of protrusions configured to engage bone material of the rib 1005 containing the medullary canal 1015.

In another optional embodiment, method 900 includes retracting the catheter through the medullary canal 1015 and out of the first access hole 1000. Then a plug 1030 is advanced over a free end 1021 of the guidewire 1020 and along the guidewire 1020 to the first access hole 1000. And then placing the guidewire 1020 under tension. Application of tension to the guidewire 1020 imparts a degree of reduction, compression and stabilization of the fracture 1010.

In one optional embodiment the guidewire 1020 is threaded, and advancing the plug 1030 down the free end 1021 of the guidewire 1020 and along the guidewire 1020 to the first access hole 1000 includes rotating the plug 1030 about the guidewire 1020 and screwing the first plug 1030 into bone defining the first access hole 1000.

In one optional embodiment, the guidewire 1020 has a diameter ranging from 1 mm to 10 mm.

In another optional embodiment, the method 900 includes sizing the medullary canal 1015 by displacing contents 1016 of the medullary canal 1015 such that the medullary canal 1015 has a diameter of at least 2 mm. In a further embodiment, sizing the medullary canal 1015 by displacing the contents 1016 of the medullary canal 1015 includes one or more of compressing, flushing or reaming one or more of the marrow or the bone.

In one optional embodiment, the first access hole 1000 is at least 10 mm from the fracture 1010. In another example embodiment, the first access hole is arranged at an acute angle relative to the medullary canal 1015, the acute angle ranging from 10 to 70 degrees. In another optional embodiment, the first access hole 1000 is located a distance away from the fracture 1010 and the fracture 1010 is either located beneath a scapula or the fracture is a paravertebral fracture (see, e.g., FIG. 28).

In one optional embodiment, manipulating the rib 1005 to realign the medullary canal 1015 across the fracture 1010.

Figure 29:
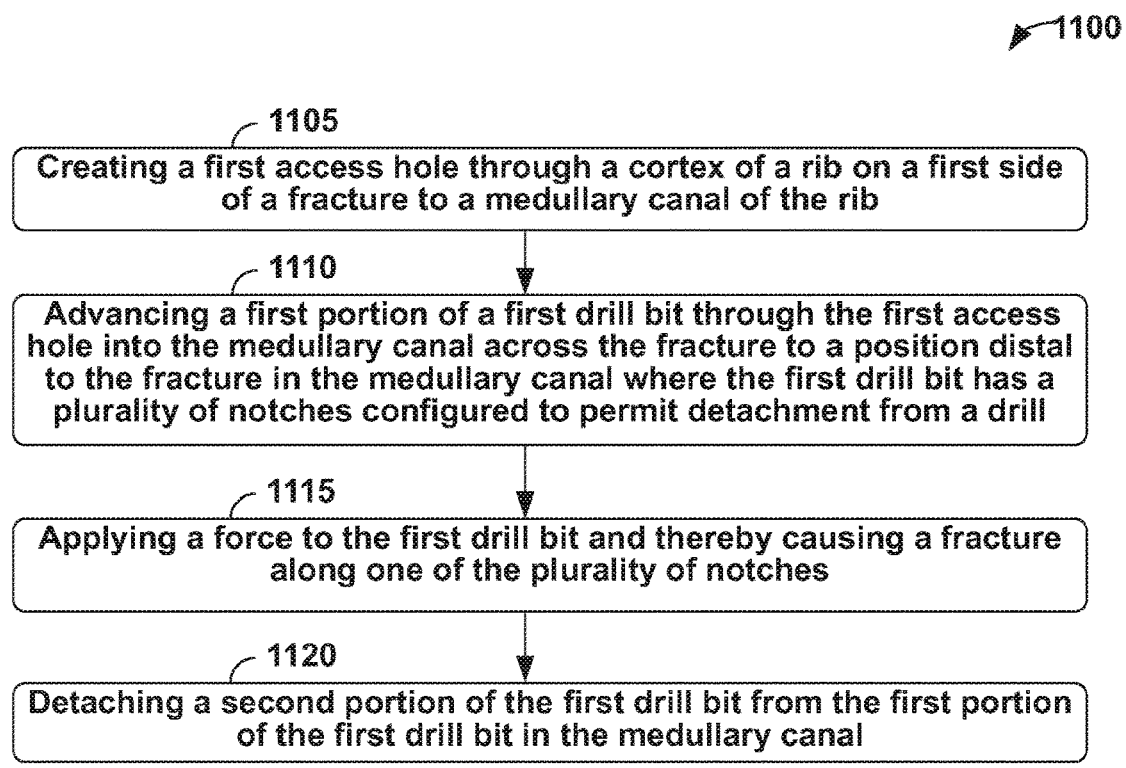
FIG. 29 shows a flowchart of a method, according to an example implementation.
Figure 30:
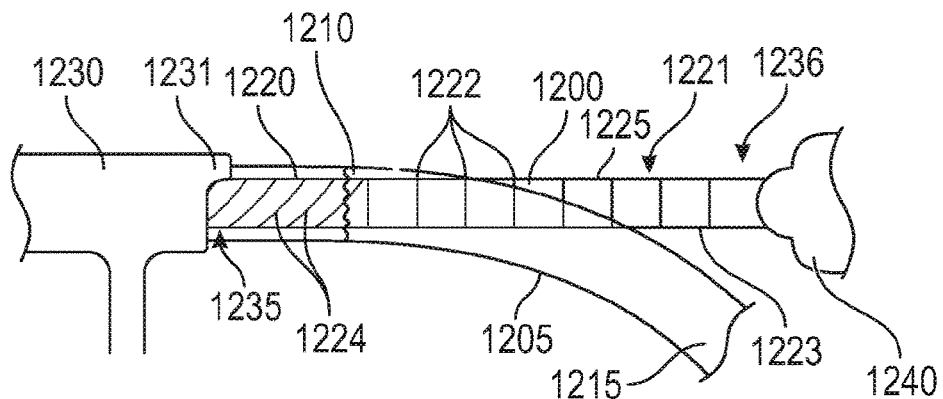
FIG. 30 shows a side cross-sectional view of a rib with a drill bit disposed therein according to one aspect of the method of FIG. 29.

Referring now to FIG. 29, a method 1100 is illustrated using various elements shown in FIG. 30. Method 1100 includes, at block 1105, creating a first access hole 1200 through a cortex of a rib 1205 on a first side of a fracture 1210 to a medullary canal 1215 of the rib 1205. Then, at block 1110, a first portion 1220 of a first drill 1221 bit is advanced through the first access hole 1200 into the medullary canal 1215 across the fracture 1210 to a position distal to the fracture in the medullary canal 1215 where the first drill bit 1221 has a plurality of notches 1222 configured to permit detachment from a drill. A force is applied to the first drill bit 1221 and thereby causes a fracture 1225 along one of the plurality of notches 1222, block 1115. And a second portion 1223 of the first drill bit 1221 detaches from the first portion 1220 of the first drill bit 1221 in the medullary canal 1215.

In one optional embodiment, the first access hole 1200 is created via a second rigid drill bit. In an alternative embodiment, the first access hole 1200 is created via the first drill bit.

In one optional embodiment, the fracture 1225 along one of the plurality of notches 1222 occurs adjacent to the first access hole 1200.

As shown in FIG. 30, in one optional embodiment, the position distal to the fracture 1210 in the medullary canal 1215 is adjacent to a vertebra 1230 or is subscapular. In one further embodiment, method 1100 includes advancing the first portion 1220 of the first drill bit 1221 out of the cortex of the bone and into a transverse process 1231 of the vertebra.

In one optional embodiment, the force applied to the first drill bit 1221 is a transverse force.

In one example embodiment, the first drill bit 1221 has a lumen extending from a first end to a second end and method 1100 includes injecting bone cement through the lumen at the second end 1236 and out of the first end 1235 of the first drill bit 1221 and into the medullary canal 1215.

In one optional example, the first drill bit 1221 is in the form of a reamer. In another example embodiment, the first drill bit 1221 includes metal or plastic.

In one optional embodiment, the first portion 1220 of the first drill bit 1221 has cutting edges 1224 and the plurality of notches 1222 are arranged every 5 mm to 10 mm along a length of the second portion 1223 of the first drill bit 1221.

An apparatus, shown in FIG. 30, that is utilized by method 1100 includes a drill bit 1221 having a first portion 1220 and a second portion 1222. The first portion 1220 of the drill bit 1221 has threads 1224 disposed along a length of the first portion 1220. The second portion 1223 of the drill bit 1221 has a plurality of notches 1222 along a length of the second portion 1223. The plurality of notches 1222 are configured to permit detachment from a drill 1240 upon application of a force to the drill bit 1221 such that a fracture 1225 is caused along one of the plurality of notches 1222. The first portion 1220 of the drill bit 1221 and one or more notches 1222 of the second portion 1223 of the drill bit 1221 are configured to remain in a medullary canal 1215 of a rib 1205.

In one optional embodiment, the first drill bit 1221 has a lumen extending from a first end 1235 to a second end 1236, the lumen configured to receive bone cement through the lumen at the second end 1236 and out of the first end 1235 of the first drill bit 1221 and into the medullary canal 1215 of the rib 1205.

In one optional embodiment, the first drill bit 1221 is in the form of a reamer.

In another example embodiment, the first drill bit 1221 includes metal or plastic. In a further example, the first portion 1220 of the first drill bit 1221 has cutting edges 1224 and the plurality of notches 1222 are arranged every 5 mm to 10 mm along the length of the second portion 1223 of the first drill bit 1221.

Figure 31:
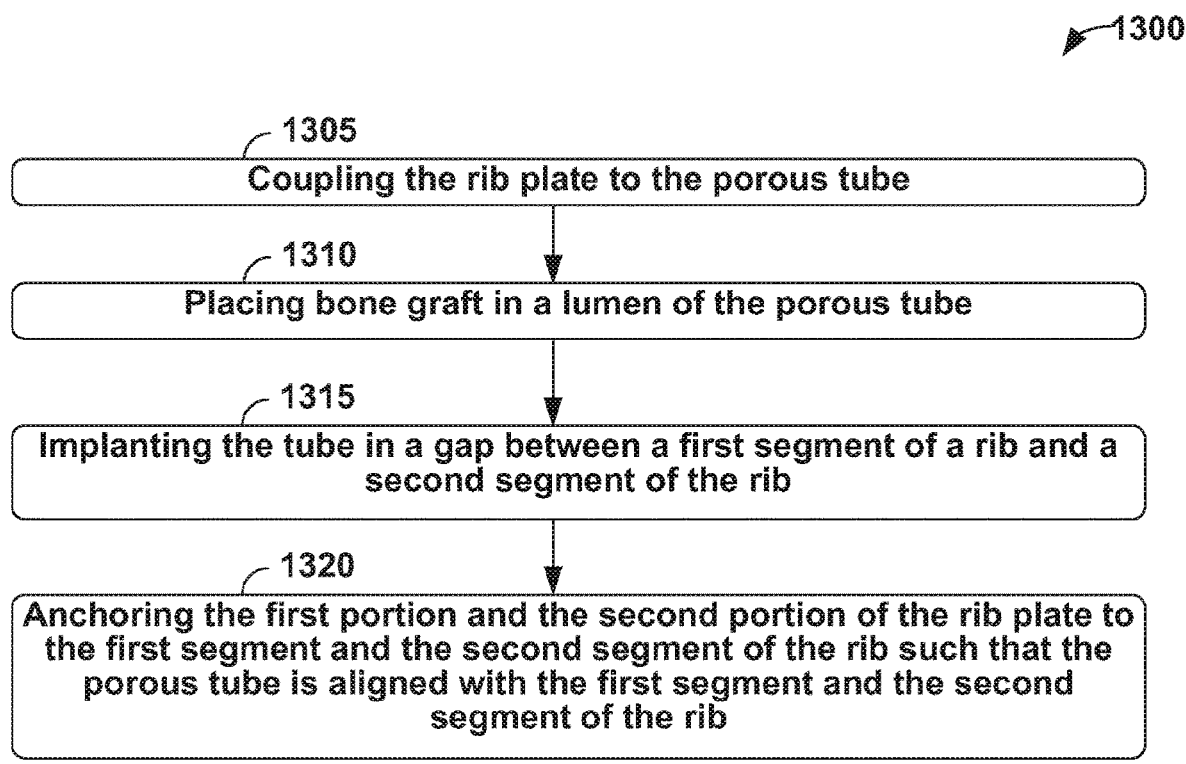
FIG. 31 shows a flowchart of a method, according to an example implementation.
Figure 32:
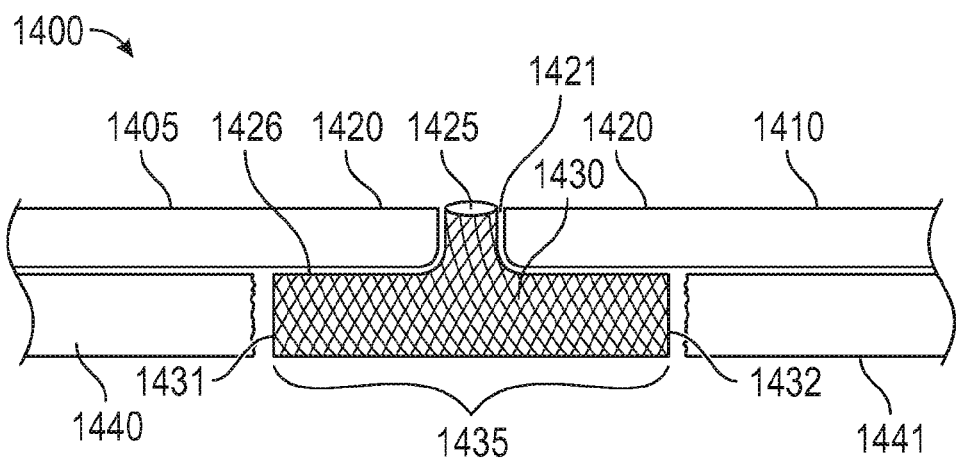
FIG. 32 shows a side view of a rib coupled to a rib plate with a porous tube disposed between a first segment and a second segment of the rib according to one aspect of the method of FIG. 31.
Figure 33:
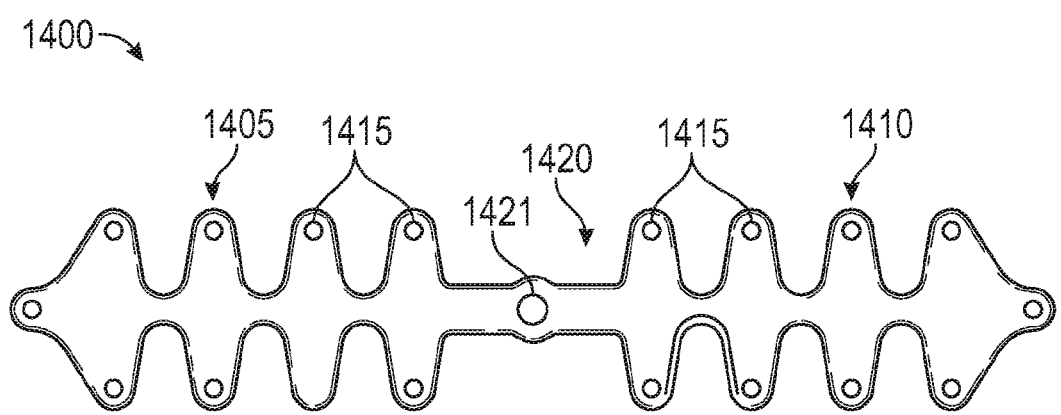
FIG. 33 shows a top view of an example rib plate according to an example implementation.

Referring now to FIG. 31, a method 1300 is illustrated using various elements shown in FIGS. 32-33. Method 1300 is for placement of a rib plate 1400 having a first portion 1405 and a second portion 1410 each having a plurality of holes 1415 therethrough and a third portion 1420 arranged between the first portion 1405 and the second portion 1410, the third portion 1420 of the rib plate 1400 having a hole 1421 configured to receive a protuberance 1425 coupled to a porous tube 1430 that has two open ends 1431, 1432. Method 1300 includes, at block 1305, coupling the rib plate 1400 to the porous tube 1430. Then, at block 1310, bone graft is placed in a lumen of the porous tube 1430. Next, at block 1315, the porous tube 1430 is implanted in a gap 1435 between a first segment of a rib 1440 and a second segment 1441 of the rib. And, at block 1320, the first portion 1405 and the second portion 1410 of the rib plate 1400 are anchored to the first segment 1440 and the second segment 1441 of the rib such that the porous tube 1430 is aligned with the first segment 1440 and the second segment 1441 of the rib.

In one optional embodiment, method 1300 includes cutting the porous tube 1430 to correspond to a length of the gap 1435 between the first segment 1405 and the second segment 1410 of the rib.

In another optional embodiment, method 1300 includes placing the bone graft in the lumen of the porous tube 1430 after coupling the rib plate 1400 to the porous tube 1430. In an alternative embodiment, method 300 includes placing the bone graft in the lumen of the porous tube 1430 prior to coupling the rib plate 1400 to the porous tube 1430 coupling the rib plate to the porous tube comprises pressing the protuberance of the tube into the hole of the third portion of the rib plate.

In one optional embodiment, the third portion 1420 of the rib plate 1400 has a length that corresponds to a length of the gap 1435 between the first segment 1440 and the second segment 1441 of the rib. In another example embodiment, the third portion 1420 of the rib plate 1400 has a width shorter than a width of either of the first portion 1405 or the second portion 1410 of the rib plate 1400.

In one optional embodiment, the porous tube 1430 includes a metal alloy or bio-absorbable material. In another example embodiment, the porous tube 1430 includes a polygonal or circular cross-section.

In one optional embodiment, prior to implanting the porous tube 1430 in the gap 1435 between the first segment 1440 of the rib and the second segment 1441 of the rib removing one or more bone fragments from between the first segment 1440 and the second segment 1441 of the rib.

In one optional embodiment, method 1300 includes anchoring the first portion 1440 and the second portion 1441 of the rib plate to the first segment 1440 and the second segment 1441 of the rib such that the porous tube 1430 is aligned with the first segment 1440 and the second segment 1441 of the rib comprises deploying each of a plurality of anchors through one of the plurality of holes 1415 in the first portion 1405 and the second portion 1410 of the rib plate 1400.

In one optional embodiment, method 1300 includes fusing the bone graft to the first segment 1440 and the second segment 1441 of the rib. In this embodiment, the bone graft will replace lost bone and augment the structural support of the rib plate 1400 across the gap 1435.

A system, shown in FIGS. 32-33, that is utilized by method 1300 includes a rib plate 1400 having a first portion 1405 and a second portion 1410 each having a plurality of holes 1415 therethrough and a third portion 1420 arranged between the first portion 1405 and the second portion 1410. The system also includes a porous tube 1430 that has two open ends 1431, 1432 and a protuberance 1425 arranged between the two ends 1431, 1432 that extends from an exterior surface 1426 of the porous tube 1430. The third portion 1420 of the rib plate 1400 has a hole 1421 configured to receive the protuberance 1425 of the porous tube 1430. And the system includes bone graft disposed in a lumen of the porous tube 1430.

In one optional embodiment, the porous tube 1430 is configured to be sized to correspond to a length of a gap 1435 between a first segment 1440 and a second segment 1441 of a rib.

In another optional embodiment, the protuberance 1425 has a diameter larger than a diameter of the hole 1421 in the third portion 1420 of the rib plate 1400. In another example embodiment, the protuberance 1425 and the hole 1421 of the third portion 1420 of the rib plate 1400 have reciprocal mating features to retain the protuberance 1425 within the hole 1421 of the third portion 1420 of the rib plate 1400. In a further embodiment, the reciprocal mating features are in the form of a rib and a groove or two ribs.

In another example embodiment, the third portion 1420 of the rib plate 1400 has a length that corresponds to a length of a gap 1435 between a first segment 1440 and a second segment 1441 of a rib. In one optional embodiment, the third portion 1420 of the rib plate 1400 has a width shorter than a width of either of the first portion 1405 or the second portion 1410 of the rib plate 1400.

In one optional embodiment, the porous tube 1430 includes a metal alloy or bio-absorbable material. In another example embodiment, the porous tube 1430 includes a polygonal or circular cross-section.

The description of different advantageous arrangements has been presented for purposes of illustration and description, and is not intended to be exhaustive or limited to the examples in the form disclosed. Many modifications and variations will be apparent to those of ordinary skill in the art. Further, different advantageous examples may describe different advantages as compared to other advantageous examples. The example or examples selected are chosen and described in order to best explain the principles of the examples, the practical application, and to enable others of ordinary skill in the art to understand the disclosure for various examples with various modifications as are suited to the particular use contemplated.

The invention claimed is:

1. A system, comprising:
    a tension line having a removable snare at a free end, wherein the tension line has threads;
    a first plug configured to be advanced down the free end of the tension line and a second access hole of a rib, wherein the first plug has a hole extending longitudinally therethrough that has reciprocal threads to mate with the threads of the tension line;
    a plurality of stents configured to be advanced over the tension line through a first access hole in the rib into a medullary canal of the rib until a length of the medullary canal between the first access hole and the second access hole is filled with the plurality of stents, wherein each of the plurality of stents has a concave face at a first end and a convex face at a second end such that, when the plurality of stents are arranged adjacent to each other along the tension line, the concave face of the first end of a first stent will mate with the convex face of the second end of an adjacent second stent; and
    a second plug configured to be advanced down an end of the tension line and into the first access hole, wherein the second plug has a hole extending longitudinally therethrough that has reciprocal threads to mate with the threads of the tension line.

2. The system of claim 1, wherein an extramedullary side of the first plug has a diameter ranging from 6 mm to 8 mm and an intramedullary side of the first plug has a diameter ranging from about 4 mm to 5 mm.

3. The system of claim 1, wherein walls extending between an extramedullary side and an intramedullary side of the first plug are concave.

4. The system of claim 1, wherein the tension line has a diameter ranging from 1 mm to 10 mm.

5. The system of claim 1, wherein the plurality of stents each have a circular cross-section and a diameter ranging from 1 mm to 5 mm.

6. The system of claim 1, wherein the plurality of stents each have an oval cross-section with a minor axis ranging from 2 mm to 5 mm and a major axis ranging from 3 mm to 8 mm.

7. The system of claim 1, wherein the plurality of stents each have a length ranging from 3 mm to 10 mm.

8. The system of claim 1, wherein the second plug has an extramedullary side that is flat and an intramedullary side that is convex.

9. A method, comprising:
    accessing a medullary canal of a rib having a fracture;
    advancing a guidewire into the medullary canal across the fracture;
    advancing a delivery catheter containing a stent over the guidewire into the medullary canal and across the fracture;
    retracting the delivery catheter relative to the stent; and
    expanding the stent in the medullary canal; and
    sizing the medullary canal by displacing contents of the medullary canal such that the medullary canal has a diameter of at least 3 mm,
    wherein sizing the medullary canal by displacing the contents of the medullary canal comprises:
        advancing a catheter containing a drill bit through an access hole to the medullary canal;

advancing the drill bit out of a first end of the catheter;

activating the drill bit thereby causing the drill bit to rotate;

advancing the contents from the medullary canal into the catheter via the rotating drill bit; and retracting the drill bit into the catheter and advancing the drill bit and the contents from the medullary canal out of an access port at a second end of the catheter.

10. The method of claim 9, wherein sizing the medullary canal by displacing the contents of the medullary canal comprises one or more of compressing, flushing or reaming one or more of a marrow or a bone.

11. The method of claim 9, further comprising:

leaving the catheter in place in the medullary canal after retraction of the drill bit.

12. The method of claim 9, wherein advancing the guidewire into the medullary canal across the fracture comprises advancing the guidewire through the catheter in the medullary canal after retraction of the drill bit.

13. The method of claim 9, wherein accessing a medullary canal of a rib having a fracture comprises:

creating an incision in a skin of a subject;

performing blunt dissection down to the rib; and drilling a hole through a cortex of the rib on one side of the fracture thereby creating an access hole to the medullary canal.

14. A method, comprising:

creating a first access hole through a cortex of a rib on a first side of a fracture to a medullary canal of the rib;

accessing the medullary canal through the first access hole;

advancing a catheter through the first access hole into the medullary canal across the fracture to a distal end of the medullary canal; and advancing a guidewire through the catheter distal to the fracture in the medullary canal and securing an anchor coupled to a distal end of the guidewire within the medullary canal, wherein the guidewire is configured as a tension line;

retracting the catheter through the medullary canal and out of the first access hole;

advancing a plug over a free end of the guidewire and along the guidewire to the first access hole; and placing the guidewire under tension.

15. The method of claim 14, wherein the anchor is expandable and comprises a stent or a plurality of radially extending barbs, wherein the anchor is configured to be self-expanding or balloon-expandable.

16. The method of claim 14, wherein the anchor is manually expandable and has a plurality of protrusions configured to engage bone material of the rib containing the medullary canal.

17. The method of claim 14, wherein the guidewire is threaded, wherein advancing the plug down the free end of the guidewire and along the guidewire to the first access hole comprises rotating the plug about the guidewire and screwing the first plug into bone defining the first access hole.

* * * * *